United States Patent
Bendory et al.

(10) Patent No.: US 10,258,225 B2
(45) Date of Patent: Apr. 16, 2019

(54) PARANASAL SINUS ACCESS SYSTEM

(71) Applicant: 3NT MEDICAL LTD., Rehovot (IL)

(72) Inventors: Ehud Bendory, Herzliya (IL); Eran Bendory, Maccabim-Reut (IL); Naveh D. Shetrit, Tel-Aviv (IL)

(73) Assignee: 3NT MEDICAL LTD., Rosh Ha'Ayin (IL)

( * ) Notice: Subject to any disclaimer, the term of this patent is extended or adjusted under 35 U.S.C. 154(b) by 505 days.

(21) Appl. No.: 14/440,760

(22) PCT Filed: Nov. 7, 2013

(86) PCT No.: PCT/IL2013/050916
§ 371 (c)(1),
(2) Date: May 5, 2015

(87) PCT Pub. No.: WO2014/072977
PCT Pub. Date: May 15, 2014

(65) Prior Publication Data
US 2015/0289754 A1     Oct. 15, 2015

Related U.S. Application Data

(60) Provisional application No. 61/900,407, filed on Nov. 6, 2013, provisional application No. 61/723,329, filed on Nov. 7, 2012.

(51) Int. Cl.
*A61B 1/00*     (2006.01)
*A61B 1/018*    (2006.01)
(Continued)

(52) U.S. Cl.
CPC .............. *A61B 1/018* (2013.01); *A61B 1/005* (2013.01); *A61B 1/00078* (2013.01);
(Continued)

(58) Field of Classification Search
CPC ...... A61B 17/3421; A61B 2017/00331; A61B 2017/3443; A61B 2017/00991
See application file for complete search history.

(56) References Cited

U.S. PATENT DOCUMENTS

| | | | |
|---|---|---|---|
| 5,231,989 A | 8/1993 | Middleman et al. | |
| 5,318,528 A | 6/1994 | Heaven et al. | |
| (Continued) | | | |

FOREIGN PATENT DOCUMENTS

| | | |
|---|---|---|
| CN | 101351236 | 1/2009 |
| DE | 4223897 | 1/1994 |
| (Continued) | | |

OTHER PUBLICATIONS

International Search Report filed in PCT/IL2013/050916, dated Mar. 4, 2014, 3 pgs.

(Continued)

*Primary Examiner* — Alexandra L Newton
(74) *Attorney, Agent, or Firm* — Merchant & Gould P.C.

(57) ABSTRACT

A device, including a straight support element, a curved support element slidably coupled to the straight support element, and a rigid straight support element slidably coupled to the curved support element, the straight support element having a first rigidity, the curved support element having a curved portion having a second rigidity greater than the first rigidity, the rigid straight support element having a third rigidity greater than the second rigidity, when the rigid straight support element overlaps the curved portion of the curved support element an overlapped portion of the curved portion conforms to a straight shape of the rigid straight support element, when the curved portion overlaps the straight support element, an overlapped portion of the (Continued)

straight support element conforms to a curved shape of the curved portion, the curved portion having a rectangular cross section.

6 Claims, 17 Drawing Sheets

(51) Int. Cl.
| | | |
|---|---|---|
| A61B 17/24 | (2006.01) | |
| A61B 17/00 | (2006.01) | |
| A61B 1/005 | (2006.01) | |
| A61B 1/012 | (2006.01) | |
| A61B 1/015 | (2006.01) | |
| A61B 1/05 | (2006.01) | |
| A61B 1/07 | (2006.01) | |
| A61B 1/233 | (2006.01) | |
| A61B 1/32 | (2006.01) | |
| A61B 5/00 | (2006.01) | |
| A61B 8/12 | (2006.01) | |
| A61B 17/30 | (2006.01) | |
| A61F 13/38 | (2006.01) | |
| A61M 25/01 | (2006.01) | |
| A61M 25/09 | (2006.01) | |

(52) U.S. Cl.
CPC .......... *A61B 1/00082* (2013.01); *A61B 1/015* (2013.01); *A61B 1/0125* (2013.01); *A61B 1/05* (2013.01); *A61B 1/07* (2013.01); *A61B 1/233* (2013.01); *A61B 1/32* (2013.01); *A61B 5/0086* (2013.01); *A61B 5/6852* (2013.01); *A61B 8/12* (2013.01); *A61B 17/00234* (2013.01); *A61B 17/24* (2013.01); *A61B 17/30* (2013.01); *A61F 13/38* (2013.01); *A61M 25/0102* (2013.01); *A61M 25/09* (2013.01); *A61B 2017/0034* (2013.01); *A61B 2017/00292* (2013.01); *A61B 2017/00331* (2013.01); *A61B 2017/00336* (2013.01); *A61B 2017/00867* (2013.01); *A61M 25/0152* (2013.01)

(56) References Cited

U.S. PATENT DOCUMENTS

| | | | |
|---|---|---|---|
| 5,788,713 A | | 8/1998 | Dubach et al. |
| 6,146,373 A | | 11/2000 | Cragg et al. |
| 6,251,115 B1 | | 6/2001 | Williams et al. |
| 6,589,251 B2 | * | 7/2003 | Yee .................. A61F 2/95 |
| | | | 604/523 |
| 6,743,239 B1 | | 6/2004 | Kuehn et al. |
| 6,743,243 B1 | | 6/2004 | Roy et al. |
| 6,860,849 B2 | | 3/2005 | Matsushita et al. |
| 7,625,356 B2 | | 12/2009 | Mickley |
| 7,678,099 B2 | | 3/2010 | Ressemann et al. |
| 8,025,635 B2 | | 9/2011 | Eaton et al. |
| 8,241,266 B2 | | 8/2012 | Keith et al. |
| 8,303,640 B2 | | 11/2012 | Hepworth et al. |
| 8,414,473 B2 | | 4/2013 | Jenkins et al. |
| 8,801,670 B2 | | 8/2014 | Drontle et al. |
| 8,858,974 B2 | | 10/2014 | Eaton et al. |
| 8,905,922 B2 | | 12/2014 | Makower et al. |
| 8,915,938 B2 | | 12/2014 | Keith et al. |
| 9,192,490 B2 | | 1/2015 | Hepworth et al. |
| 9,044,581 B2 | | 6/2015 | Schaeffer et al. |
| 9,055,965 B2 | | 6/2015 | Chang et al. |
| 9,089,258 B2 | | 7/2015 | Goldfarb et al. |
| 9,101,384 B2 | | 8/2015 | Makower et al. |
| 9,241,834 B2 | | 1/2016 | Chang et al. |
| 9,278,199 B2 | | 3/2016 | Keith et al. |
| 9,320,876 B2 | | 4/2016 | Ressemann et al. |
| 9,440,049 B2 | | 9/2016 | Drontle et al. |
| 9,554,817 B2 | | 1/2017 | Goldfarb et al. |
| 9,585,681 B2 | | 3/2017 | Eaton et al. |
| 9,586,034 B2 | | 3/2017 | Schaeffer et al. |
| 9,592,370 B2 | | 3/2017 | Schaeffer et al. |
| 9,694,167 B2 | | 7/2017 | Keith et al. |
| 2008/0167527 A1 | | 7/2008 | Slenker et al. |
| 2008/0183128 A1 | | 7/2008 | Morriss et al. |
| 2009/0171271 A1 | | 7/2009 | Webster et al. |
| 2010/0030113 A1 | | 2/2010 | Morriss et al. |
| 2010/0076403 A1 | | 3/2010 | Harris et al. |
| 2011/0257479 A1 | | 10/2011 | Adams et al. |
| 2012/0029334 A1 | * | 2/2012 | Tegg ................ A61M 25/0136 |
| | | | 600/373 |
| 2012/0053567 A1 | | 3/2012 | Schreck et al. |
| 2012/0071857 A1 | | 3/2012 | Goldfarb et al. |
| 2014/0358177 A1 | | 12/2014 | Schreck et al. |
| 2014/0371532 A1 | * | 12/2014 | Trovato ............ A61B 17/3421 |
| | | | 600/114 |
| 2015/0141819 A1 | | 5/2015 | Linden et al. |

FOREIGN PATENT DOCUMENTS

| | | |
|---|---|---|
| DE | 4223897 A1 | 1/1994 |
| EP | 1284657 | 9/2011 |
| EP | 2121108 | 2/2012 |
| EP | 1789110 | 8/2013 |
| EP | 1879499 | 8/2014 |
| EP | 2662109 | 4/2015 |
| EP | 2618886 | 10/2015 |
| EP | 2491973 | 8/2016 |
| EP | 2185234 | 3/2017 |
| JP | H06-505188 | 6/1994 |
| JP | 2001-520085 | 10/2001 |
| JP | 2005-515830 | 6/2005 |
| JP | 2007-202727 | 8/2007 |
| JP | 2009-100929 | 5/2009 |
| JP | 2011-239989 | 12/2011 |
| WO | WO1992014506 | 9/1992 |
| WO | WO 2003063732 | 8/2003 |
| WO | WO2007059233 | 5/2007 |
| WO | 2011/064602 | 6/2011 |
| WO | 2011064602 A1 | 6/2011 |
| WO | WO2011141925 | 11/2011 |

OTHER PUBLICATIONS

International Search Report and Written Opinion dated Mar. 20, 2014 issued in connection with International Application No. PCT/IL2013/050916.

* cited by examiner

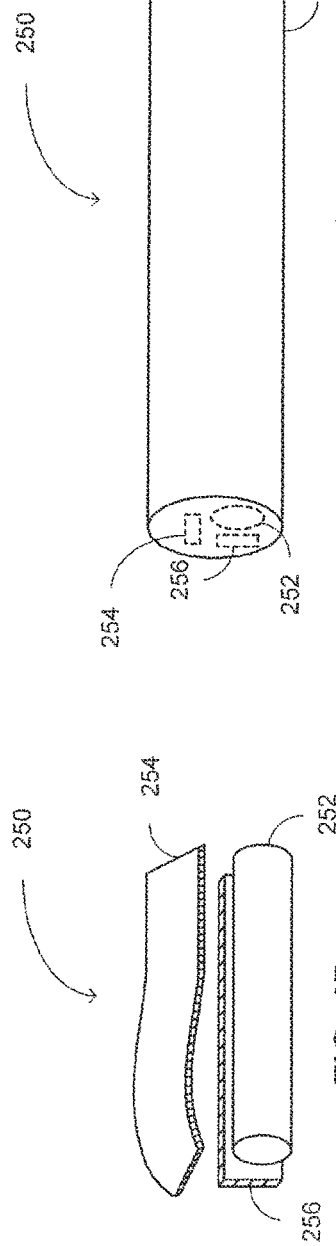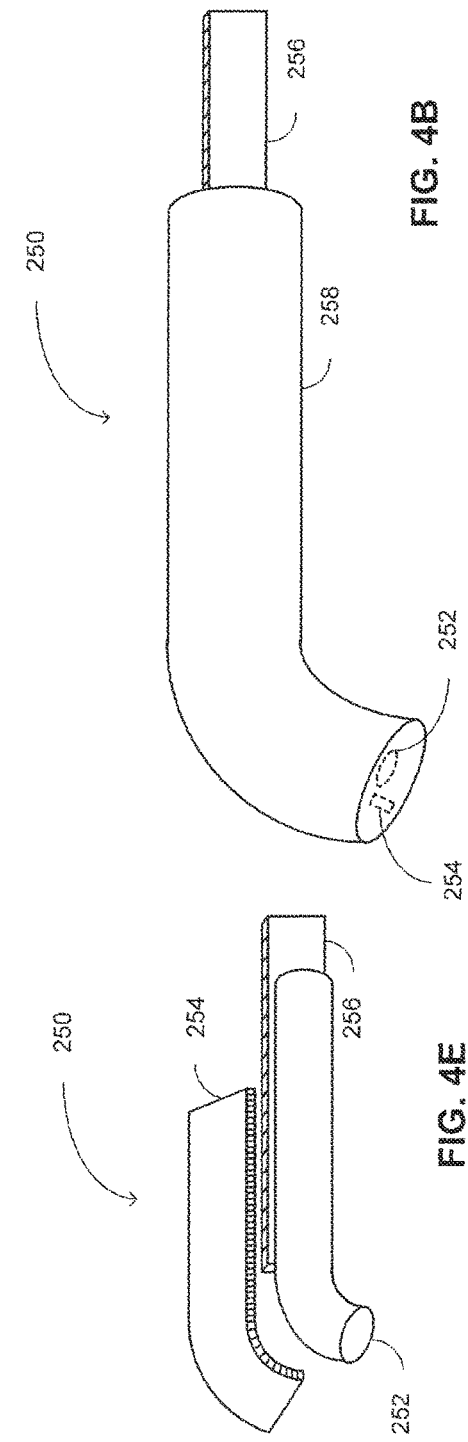

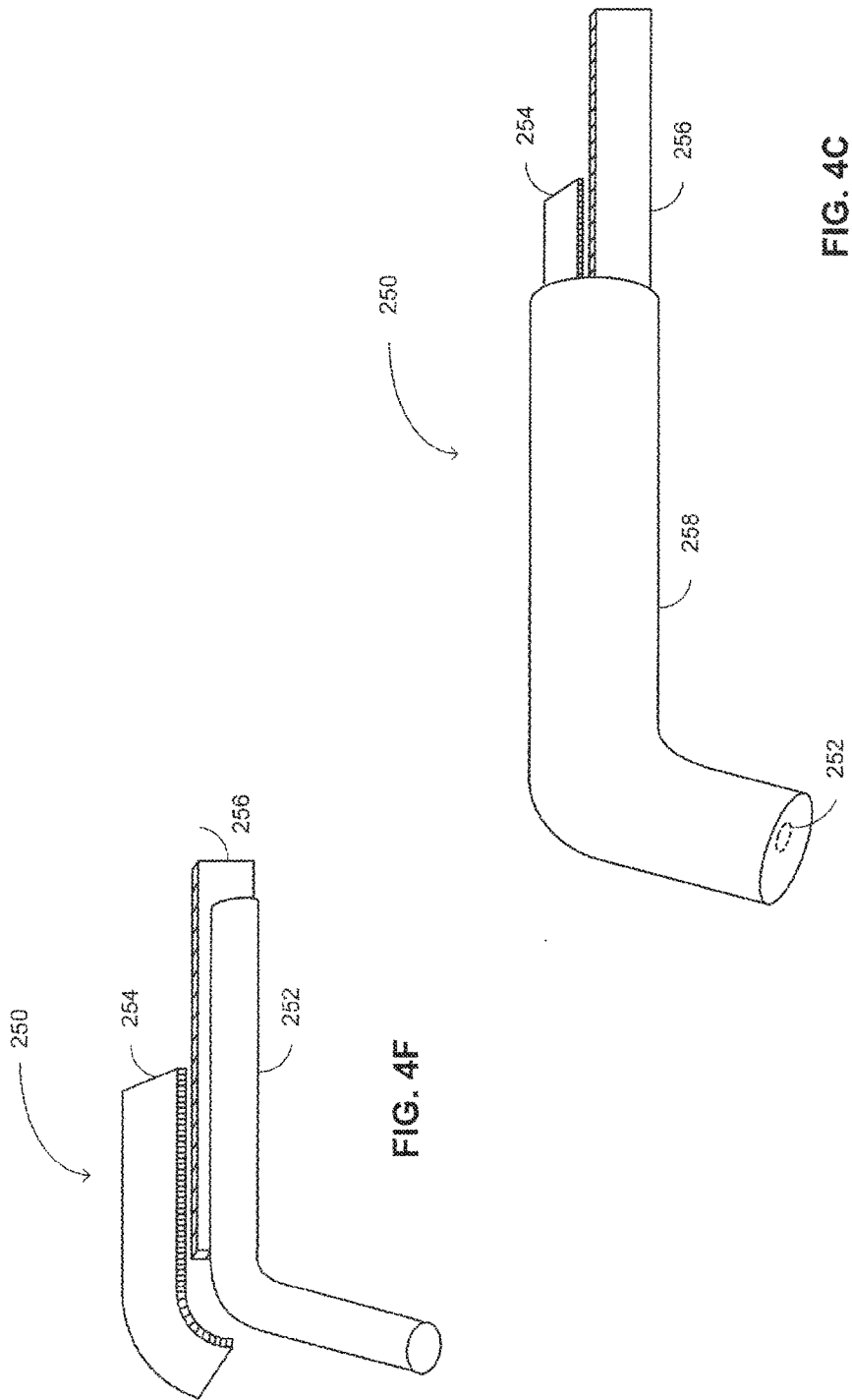

PARANASAL SINUS ACCESS SYSTEM

CROSS-REFERENCE TO RELATED APPLICATIONS

This application is a national phase application claiming priority to International Patent Application No. PCT/IL2013/050916 filed Nov. 7, 2013, which claims priority to U.S. Provisional Patent App. No. 61/900,407 filed Nov. 6, 2013 and U.S. Provisional Patent App. No. 61/723,329 filed Nov. 7, 2012, all of which are wholly incorporated herein by reference.

FILED OF THE DISCLOSED TECHNIQUE

The disclosed technique relates to access systems, in general, and to methods and systems for accessing the paranasal sinus, in particular.

BACKGROUND OF THE DISCLOSED TECHNIQUE

Functional endoscopic sinus surgery (FESS) is the most common type of surgery employed to treat chronic rhinosinusitis (CRS). In a typical FESS, an endoscope is advanced into the nasal cavities along with one or more rigid surgical instruments. The surgical instruments are then used, for example, to resect tissue, resect bone, ablate, and suction. In most FESS procedures, the natural ostium of at least one paranasal sinus is surgically enlarged to improve drainage from the sinus cavity. The endoscope provides direct visualization of most of the surgical field; however, certain anatomic structures (e.g., uncinate process, ethmoidal cells, or frontal recess) obstruct the line of sight to hidden parts of the surgical field. Moreover, anatomic variations (e.g., septal deviation) further limit the access to the area that requires treatment. Therefore, in order to adequately view the entire surgical field through the endoscope and safely remove diseased or hypertrophic tissue or bone, the physician is forced to remove or at least modify normal healthy anatomic structures thereby inflicting substantial collateral damage and trauma.

Several devices which provide less invasive treatment options are known in the art. Reference is now made to U.S. Pat. No. 6,251,115, issued to Williams et al., and entitled "Method for The Medical Treatment of The Neurological System". This publication relates to a system for the non-linear insertion of a catheter or lead into an interior organ. FIGS. 4, 5 and 6 present a co-centric tubular system for insertion of the lead. The non-linear insertion system includes a substantially linear outer tubular member, an inner tubular member, and a stylet. The stylet is slidably coupled within the inner tubular member, which in turn is slidably coupled within the outer tubular member, thereby forming a concentric system. The inner tubular member is of a curved shape and is fabricated from a superelastic material, such that it regains its curved shape when not constrained by the outer tubular member.

A surgeon inserts the outer tubular member into the organ being treated. After the outer tubular member is placed to the desired depth, the surgeon fixes its position. Next, the surgeon selectively advances the inner tubular member out the distal end of the outer tubular member. After the surgeon selectively advances the inner tubular member to the desired point along a desired curvilinear trajectory, the surgeon fixes the inner tubular member relative to the outer tubular member. Then the surgeon advances the stylet outwardly from the distal end of the inner tubular member toward the treatment site.

Reference is now made to U.S. Pat. No. 5,788,713, issued to Dubach et al., and entitled "Method and Apparatus for Stereotactic Implantation". This publication relates to a device for the percutaneous localization of a foreign object in a body. The device includes a guide-tube cannula, a curved nitinol tubing, and a nitinol wire. The nitinol wire is slidably coupled within the curved nitinol tubing, which in turn is slidably coupled within the guide-wire cannula. The cannula and the wire are substantially straight. The curved tubing is curved. When the curved tubing protrudes out of the cannula, the tubing regains its original curved shape. When the wire protrudes out of the curved tubing it regains its original straight shape. Thereby, the wire of the implementation device can travel in a non-straight trajectory.

Reference is now made to U.S. Pat. No. 7,625,356, issued to Mickley, and entitled "Tortuous Path Injection Device". This publication relates to a device for delivering therapeutic or diagnostic agents to a target tissue of a human body. The device includes a sheath lumen, a first elongate shaft, and a second elongate shaft. The first elongate shaft is slidingly disposed within the sheath lumen, and the second elongate shaft is slidingly disposed within the first elongate shaft. The first elongate shaft includes a curved portion. Thereby the device defines a tortuous path.

SUMMARY OF THE PRESENT DISCLOSED TECHNIQUE

It is an object of the disclosed technique to provide a novel method and system for accessing a paranasal sinus of a patient. In accordance with an embodiment of the disclosed technique, there is thus provided a system for accessing a paranasal sinus in the head of a patient. The system includes a weak straight supporter, a curved supporter and a strong straight supporter. The curved supporter is slidably coupled with the weak straight supporter. The strong straight supporter is slidably coupled with the weak straight supporter and with the curved supporter. The curved supporter is made of a shape memory material and has a curved shape memory. The rigidity of the curved supporter exceeds that of the weak straight supporter. The rigidity of the strong straight supporter exceeds that of the curved supporter. When the strong straight supporter overlaps the curved supporter, an overlapped portion of the curved supporter conforms to the straight shape of the strong straight supporter, and when the curved supporter overlaps the weak straight supporter, an overlapped portion of the weak straight supporter conforms to the curved shape of the curved supporter In accordance with another embodiment of the disclosed technique, the curved supporter has a non-tubular cross section. For example, the curved supporter is bar shaped.

In accordance with a further embodiment of the disclosed technique, the strong straight supporter and the curved supporter have different cross sections. For example, the strong straight supporter is tube shaped and the curved supporter is bar shaped.

In accordance with yet another embodiment of the disclosed technique, the weak straight supporter and the curved supporter have different cross sections. For example, the weak straight supporter is tube shaped and the curved supporter is bar shaped.

In accordance with yet a further embodiment of the disclosed technique, the access system further includes a work channel providing passageway into and out of the sinus cavity therethrough. The strong supporter, the curved supporter and the weak supporter guide the work channel into the sinus cavity.

In accordance with yet another embodiment of the disclosed technique, upon retraction of the strong straight supporter and the curved supporter, the weak straight supporter is maintained in place enabling access to, and from, the sinus cavity therethrough (i.e., the work channel is defined as the lumen of the weak supporter).

In accordance with yet a further embodiment of the disclosed technique, the access system includes an external sheath enfolding the weak straight supporter. Upon retraction of the strong straight supporter the curved supporter, and the weak straight supporter, the external sheath is maintained in place enabling access to, and from, the sinus therethrough (i.e., the work channel is defined as the lumen of the external sheath).

In accordance with yet another embodiment of the disclosed technique, at least one of the strong straight supporter and the weak straight supporter includes one or more lumens providing passageway into and out of the sinus cavity therethrough. The curved supporter, strong straight supporter and weak supporter are maintained in place enabling access to, and from, the sinus cavity therethrough (i.e., the work channel is defined as the one or more lumens of the strong straight and weak straight supporters). Thereby, there is no need to retract the access system to enable access to, and from, the sinus therethrough.

In accordance with yet a further embodiment of the disclosed technique, the curved supporter includes a pull wire sliding along its perimeter and extending proximally out of the body of the patient. The curved supporter is curving when the pull wire is pulled. It is noted that only the curved wire includes a pull wire and specifically neither the strong supporter, nor the weak supporter, include a pull wire.

In accordance with yet another embodiment of the disclosed technique, the access system further includes a functional distal head. The distal head is coupled to the distal end of the weak straight supporter.

In accordance with yet a further embodiment of the disclosed technique, the functional distal head is coupled to a camera for acquiring images from the way into, or from within, the paranasal sinus.

In accordance with yet another embodiment of the disclosed technique, the camera is positioned on a front surface of the functional distal head.

In accordance with yet a further embodiment of the disclosed technique, the camera is coupled with wires (i.e., camera wires) for transferring image signals produced by the camera. The camera wires are coupled to an inner wall of the weak supporter, and in particular, to the wall that is closer to the curve of the access system. That is, the camera wires are coupled to the intrados side of the inner wall (i.e., inner surface) of the weak supporter. Alternatively, the camera wires are coupled to the intrados surface of an enfolding sleeve, or an external sheath, of the access system.

In accordance with yet another embodiment of the disclosed technique, the functional distal head is coupled to one or more illuminating devices illuminating the surrounding of the functional distal head. The illuminating devices can include for example, optical fibers, fiber bundles, optical elements such as lenses, deflectors, reflectors, prisms, and the like.

In accordance with yet a further embodiment of the disclosed technique, the illuminating devices can include between 1-6 optical fibers, which can be grouped (i.e., one or more groups) or separated.

In accordance with yet another embodiment of the disclosed technique, the illuminating devices can include one or more optical bundles. For example, the illuminating device includes a single optical bundle, or two optical bundles positioned at opposite ends of the cross section of the access system.

In accordance with yet a further embodiment of the disclosed technique, the illuminating device is coupled to at least one wire for powering thereof. The powering wires are positioned at, or toward, the intrados of the weak supporter.

In accordance with yet another embodiment of the disclosed technique, the illuminating device includes optical fibers positioned at, or toward, the intrados of the weak supporter.

In accordance with yet a further embodiment of the disclosed technique, the functional distal head of the access system includes one or more ports. The ports are coupled to respective passageways (e.g., lumens, tubes, channels, conduits, ducts, or channels).

In accordance with yet another embodiment of the disclosed technique, the one or more ports of the functional distal head are configured for transferring fluids therethrough from a container, via the respective passageways to the paranasal sinus.

In accordance with yet a further embodiment of the disclosed technique, the one or more ports of the functional distal head are configured for providing fluids for washing a surface of a camera installed at the functional distal head.

In accordance with yet another embodiment of the disclosed technique, the one or more ports of the functional distal head are for transferring fluids therethrough from the paranasal sinus, via the respective passageways to an external container.

In accordance with yet a further embodiment of the disclosed technique, the access system is operable by using a single hand (i.e., single handed operation).

In accordance with yet another embodiment of the disclosed technique, the outer diameter of the weak supporter is equal to, or larger than, that of the curved supporter or that of the strong supporter.

In accordance with yet a further embodiment of the disclosed technique, the value of an outer diameter of the access system is continuous along the length of said system. That is, the outer diameter of the access system includes no steps, protrusions, projections, bulges, niches, niches, recess, and the like. In this manner, the damage to the surrounding tissues is reduced.

In accordance with yet another embodiment of the disclosed technique, there is thus provided a method for accessing a paranasal sinus of a patient, the method includes the steps of inserting a strong straight supporter of an access system to a first position, advancing a curved supporter of the access system beyond the strong supporter, and advancing a weak straight supporter of the access system beyond the curved supporter. The curved supporter is slidably coupled with the strong straight supporter. The curved supporter is made of a shape memory material and has a curved shape memory. The rigidity of the curved supporter is lower than that of the strong straight supporter. The weak straight supporter is slidably coupled with the curved supporter. The rigidity of the weak straight support is lower than that of the curved supporter.

In accordance with yet a further embodiment of the disclosed technique, a portion of the curved supporter that overlaps the strong supporter, conforms to the straight shape of the strong straight supporter.

In accordance with yet another embodiment of the disclosed technique, a portion of the weak supporter that overlaps the curved supporter, conforms to the shape (e.g., curved) of the curved supporter.

In accordance with yet a further embodiment of the disclosed technique, a portion of the weak supporter that does not overlap with the curved supporter, conforms to a substantially straight shape.

In accordance with yet another embodiment of the disclosed technique, when the weak supporter reaches a desired destination within the sinus cavity, at least one of the curved supporter and the strong supporter can be retracted from the body of the patient. In this manner, the vacated space within the access system can be employed for accessing the sinus cavity (e.g., inserting working tools into the sinus cavity).

In accordance with yet a further embodiment of the disclosed technique, the sinus access method further includes the step of inserting a working tool into the paranasal sinus through a work channel defined within the weak supporter.

In accordance with yet another embodiment of the disclosed technique, the working tool is a tool selected from the list consisting of: a camera, one or more optical fibers, one or more fiber bundles, a swab, a pair of tweezers, a suction tube, an irrigation tube, an injection tube, a balloon, an ultrasound probe, an ultrasound waveguide, an infrared imaging device, a probe, a sensor, a stylet, and a guide wire.

In accordance with yet a further embodiment of the disclosed technique, the working tool is employed for performing an action selected from the list consisting of: acquiring an image of the sinus, illuminating the sinus, collecting tissue sample, performing suction from the sinus, irrigating the sinus, injecting fluids into the sinus, delivering a drug into the sinus, dilating a balloon in or near the sinus, acquiring an ultrasound image of the sinus, acquiring an IR image of the sinus, irradiating the sinus with energy, and inducing power (e.g., ultrasound, IR) to the sinus.

In accordance with yet another embodiment of the disclosed technique, images of the way into the paranasal sinus, or of the interior of the paranasal sinus itself, can be acquired during advancement of the access system via a an imaging device (e.g., a camera) coupled thereto. Alternatively, the images can be acquired when the access system is not pushed into the paranasal sinus. Further alternatively, the images can be acquired only after the access system is anchored in its current position. The access system can be anchored, for example, by employing a balloon that can be inflated such that it tightly fits its surrounding tissues. In this manner, for example, the camera is anchored and stabilized during image acquisition.

In accordance with yet a further embodiment of the disclosed technique, the working tool can be washed by fluids passed via the access system. For example, a camera may become dirty during insertion into the sinus cavity, and therefore can be washed prior to acquiring images.

In accordance with yet another embodiment of the disclosed technique, there is thus provided an apparatus for providing access to a paranasal sinus. The apparatus includes a housing having a rear surface configured to be coupled to a supporter of an access system. The housing is configured to accommodate a camera for acquiring one or more images of the way into the paranasal sinus, or of the interior of the paranasal sinus itself, and one or more illuminating elements for providing illumination on the way into the paranasal sinus, or in the interior of the paranasal sinus itself.

In accordance with yet a further embodiment of the disclosed technique, the housing of the apparatus further includes at least one port enabling transfer of fluids into and out of the paranasal sinus.

In accordance with yet another embodiment of the disclosed technique, the access system enables the operator to access more than one paranasal sinus without retracting the access system from the body of the patient. For example, first the operator employs the access system to access a first paranasal sinus (e.g., the maxillary sinus cavity). After performing an action within the first paranasal sinus, the operator retracts the weak supporter (still being within the body of the patient) and either retracts or extends the curved supporter for defining a different curve angle of the access system for accessing a second paranasal sinus (e.g., the frontal sinus cavity). Additionally, after retracting the weak supporter and before accessing the second paranasal sinus, the operator can rotate the access system for accessing the second paranasal sinus.

In accordance with yet a further embodiment of the disclosed technique, there is thus provided a method for accessing a position near or within a paranasal sinus. The method includes the steps of advancing a first supporter into the nasal cavity, and advancing a second supporter, slidably coupled with the first supporter, along a predetermined curvature into the paranasal sinus.

In accordance with yet another embodiment of the disclosed technique, the method for accessing a position near or within the paranasal sinus further includes the step of advancing the second supporter along a substantially straight path, after passing the predetermined curvature in the nasal cavity.

In accordance with yet a further embodiment of the disclosed technique, a third supporter is coupled to the second supporter and is capable to conform to a shape of the second supporter.

In accordance with yet another embodiment of the disclosed technique, a portion of the third supporter that does not overlap with the second supporter is capable to conform to a straight shape.

In accordance with yet a further embodiment of the disclosed technique, the method for accessing a position near or within the paranasal sinus further includes the steps of retracting at least one of the first supporter and the second supporter from the paranasal sinus, and maintaining at least a portion of the third supporter within the paranasal sinus.

In accordance with yet another embodiment of the disclosed technique, the method for accessing a position near or within the paranasal sinus further includes the step of transferring a working tool through the third supporter to the paranasal sinus.

In accordance with yet a further embodiment of the disclosed technique, the at least a portion of said third supporter is a flexible sheath. The flexible sheath is configured to enable transferring a working tool therethrough.

BRIEF DESCRIPTION OF THE DRAWINGS

The disclosed technique will be understood and appreciated more fully from the following detailed description taken in conjunction with the drawings in which:

FIGS. 4A-4C are schematic illustrations of a system, for accessing a paranasal sinus cavity of a patient, constructed and operative in accordance with yet another embodiment of the disclosed technique;

FIGS. 4D-4F are schematic illustrations of the access system of FIGS. 4A-4C, in which the external sheath is removed from the image such that the internal portions of the access system are exposed to the viewer for better clarifying the operation thereof;

DETAILED DESCRIPTION OF THE EMBODIMENTS

Figure 1A:
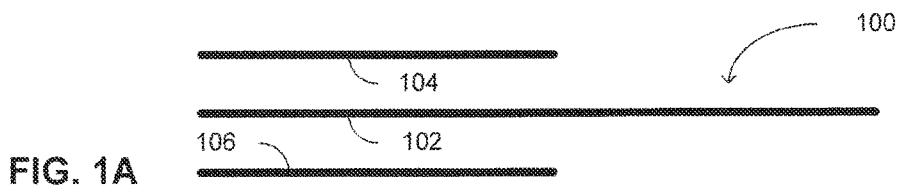
FIGS. 1A-1D are schematic illustrations of a system, for accessing a paranasal sinus cavity of a patient, constructed and operative in accordance with an embodiment of the disclosed technique.

The disclosed technique overcomes the disadvantages of the prior art by providing an access system including a straight rigid supporter, a curved semi-rigid supporter and a straight semi-rigid supporter. The rigidity of the supporters is graded in an escalating manner from the straight semi-rigid supporter, which is the least rigid, through the curved semi-rigid supporter and to the straight rigid supporter, which is the most rigid of the three. Each of the curved semi-rigid supporter and the straight semi-rigid supporter is made of a shape memory material, such that it regains its original shape after being temporarily deformed. The three supporters are slidably coupled with each other, whether directly (e.g., by sliding rails, or by being arranged in a concentric configuration), or indirectly by another component (e.g., a multilumen sheath). An operator of the access system advances the three supporters toward the sinus of a patient. At a first point, the operator holds the straight rigid supporter while continuing to advance the curved semi-rigid supporter and the straight semi-rigid supporter. At a second point, distal to the first point, the operator holds the curved semi-rigid supporter while continuing to advance the straight semi-rigid supporter until accessing the sinus. Herein below, the terms "sinus", "sinus cavity", and "paranasal sinus" may be employed interchangeably.

Reference is now made to FIGS. 1A-1D, which are schematic illustrations of a system, generally referenced 100, for accessing a paranasal sinus cavity of a patient, constructed and operative in accordance with an embodiment of the disclosed technique. Access system 100 includes a straight semi-rigid supporter 102, a curved semi-rigid supporter 104 and a straight rigid supporter 106. In the examples set forth in FIGS. 1A-1D, each of straight semi-rigid supporter 102, curved semi-rigid supporter 104 and straight rigid supporter 106 is schematically depicted as a line for explaining the mechanical principles of the disclosed technique. It is noted however, that the supporters can be of any elongated shape, such as bar shaped or tube shaped. In addition the cross section shape of each of the supporters can be any closed shape, such as a rectangle, a circle, an ellipse, a crescent and the like.

Each of the three supporters has different rigidity. In particular, the rigidity of the supporters is escalating from straight semi-rigid supporter 102, which is the least rigid, through curved semi-rigid supporter 104 to straight rigid supporter 106, which is the most rigid. Therefore, herein below straight semi-rigid supporter 102 is also referred to as weak straight supporter 102 (i.e., or simply as weak supporter), and straight rigid supporter 106 is also referred to as strong straight supporter 106 (i.e., or simply as strong supporter). Curved semi-rigid supporter is also referred to herein as a curved supporter.

The three supporters are mechanically slidably coupled with each other. The supporters can either be coupled directly, for example by sliding rails or by being arranged in a concentric configuration, or coupled via another element (e.g., by being arranged in a co-linear configuration, or in a mix of concentric and co-linear configuration, enfolded within a sheath or a sleeve). An operator of access system 100 can advance each of the supporters separately or advance all or some of the supporters together.

Each of weak straight supporter 102 and curved supporter 104 is made of a memory shape material (e.g., shape memory alloy or polymer). That is, when either one of weak straight supporter 102 or curved supporter 104 is forced to change its original shape, it retains a memory of this original shape, and returns to it once freed from the physical constraint forcing the shape change. As implied by their names, the shape memory of weak straight supporter 102 is straight, and that of curved supporter 104 is curved.

Alternatively, weak straight supporter 104 is made of a flexible or deflectable material. For example, the weak supporter can be formed from a coil enfolded by a polymeric layer (e.g., silicon, PTFE), for preventing fluids to pass through the coil and into the access system. In this manner, the weak supporter is rigid enough to push its way along the tissues of the surrounding anatomy, and is soft enough for not damaging the surrounding tissues.

Strong straight supporter 106 is made of a material which is more rigid than that of curved supporter 104, such as a metal or metal alloy (e.g., steal), a rigid polymer, and the like. While strong straight supporter is more rigid than the curved supporter and the weak supporter, according to some embodiments, it can be somewhat flexible or deflectable. Thereby, when the strong supporter is being pushed through the anatomy of the patient it can bend a little bit for enabling it to pass through more easily and without damaging the surrounding tissues (or at least reducing the damage to the surrounding tissues). Alternatively, the strong supporter can be malleable, such that the operator can form a bend along the strong supporter prior to insertion into the patient, so that the strong supporter would fit the anatomy of the patient better. For example, a somewhat flexible, or malleable, strong supporter can be employed for overcoming a deviated nasal septum anatomy.

Figure 1B:
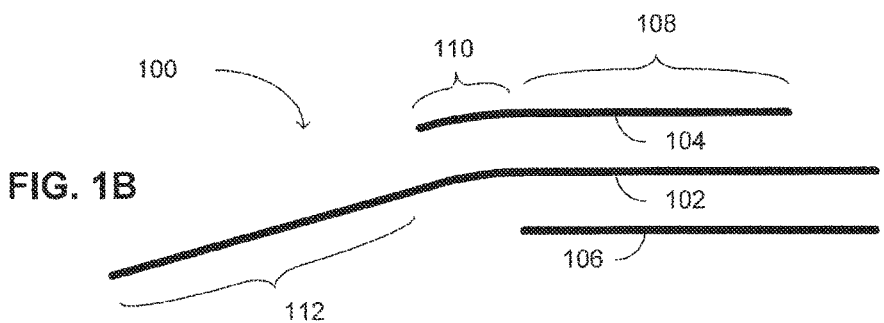
Figure 1C:
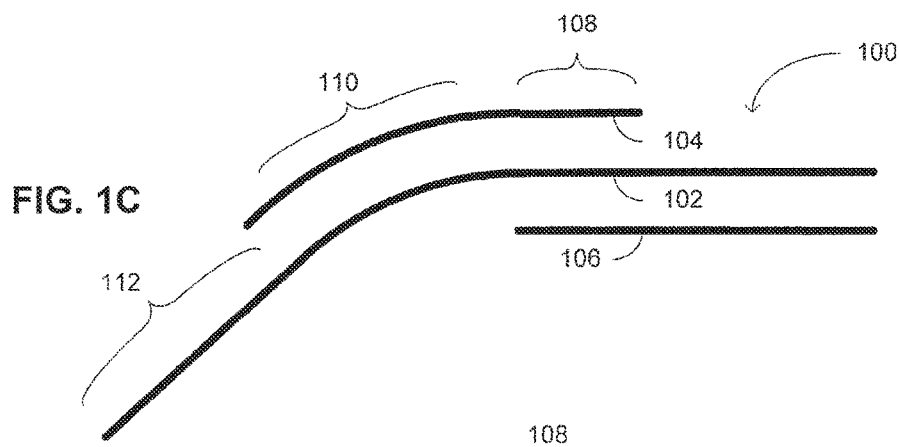
Figure 1D:
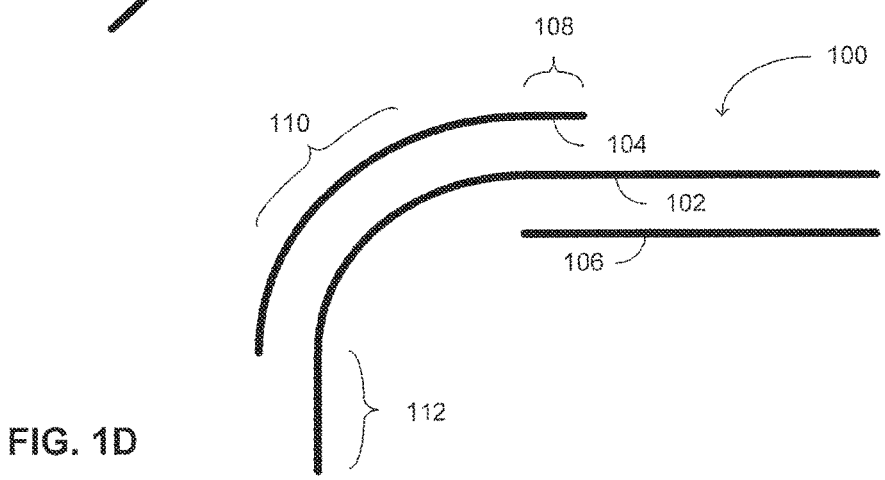

In particular, when curved supporter 104 overlaps a portion of (i.e., or all of) weak straight supporter 102, curved supporter 104 forces the overlapped portion of weak straight supporter 102 (e.g., the portion of weak straight supporter 102 which overlaps portion 110 of curved supporter 104, in FIGS. 1B-1D) to conform to the curved shape of curved semi-rigid supporter 104. However, when a portion of weak straight supporter 102 extends beyond the length of curved supporter 104, that portion of weak straight supporter 102 (e.g., portion 112 of weak straight supporter 102, of FIGS. 1B-1D) regains its straight shape.

Furthermore, when strong straight supporter 106 overlaps a portion of (i.e., or all of) curved supporter 104, strong straight supporter 106 forces the overlapped portion of curved supporter 104 (e.g., portion 108 of curved supporter 104, in FIGS. 1B-1D) to conform to the straight shape of strong straight supporter 106. However, when a portion of curved supporter 104 extends beyond the length of strong straight supporter 106, that portion of curved supporter 104 (e.g., portion 110 of curved supporter 104, of FIGS. 1B-1D) regains its curved shape.

As can be seen in FIG. 1A, strong straight supporter 106 and curved supporter 104 are fully overlapping, and therefore strong straight supporter 106 forces curved supporter 104 to conform to a straight shape. As can be seen in FIGS. 1B-1D, the curve angle of the path of access system 100 is determined by the radius of curvature of curved semi-rigid supporter 104, and by the length of portion 110 of curved supporter 104, which does not overlap strong straight supporter 106.

The curve angle (i.e., also referred to as the curvature angle) of access system 100 is defined by the angle between strong straight supporter 106 (i.e., or the portion of weak straight supporter 102, which is parallel thereto) and portion 112 of weak straight supporter 102. The radius of curvature of curved supporter 104 can be defined as the radius of an imaginary circular arc that best approximates the curve of curved supporter 104. Thus, the radius of curvature is a structural property of curved supporter 104.

Put another way, the radius of curvature of the access system is a measure of the acuteness of the bending of the access system. In particular, a small value of radius of curvature (e.g., about 2 mm) of the access system relates to an acute bend, and a larger radius of curvature value (e.g., about 5 mm) relates to a less acute bend. It is noted that the curvature of the access system does not necessarily fit a circular arc, and can fit a circular, elliptical or other non-linear arc. Thus, different sections of the curved supporter can have different radii of curvatures.

The radius of curvature of curved supporter 104, and therefore of access system 100, is predetermined and constant. On the other hand, the curve angle of access system 100 is determined by the length of curved supporter that does not overlap strong supporter 106. The length of portion 110 of curved supporter 104, which does not overlap strong supporter 106, is controlled by the operator of access system 100 (i.e., who can either push curved supporter 104 distally with respect to strong supporter 106, or pull strong supporter 106 proximally). For example, the curve angle of access system 100 is increased with the increase in the length of non-overlapping portion 110 from the length depicted in FIG. 1B, to the length depicted in FIG. 1C, and further to the length in depicted in FIG. 1D. In summary, the curve angle of access system 100 is a function of the predetermined radius of curvature of curved supporter 104, and of the length of portion 110 of curved supporter 104, as controlled by the operator. Thus, the curve angle can be dynamically determined to fit the anatomy of a specific patient.

In this manner, the operator of access system 100 controls the curve angle of access system 100 by controlling the length of portion 110 of curved supporter 104, which extends beyond strong straight supporter 106. During insertion of access system 100 into the paranasal sinus of the patient, the operator of the access system pushes all supporters together distally (i.e., in the examples set forth in FIGS. 1A-1D, the distal direction is toward the left hand side of the figure) until reaching a first point, in which a curved movement is required for accessing the sinus. The operator pushes distally both curved supporter 104 and weak straight supporter 102 (i.e., while holding strong straight supporter 106 in place) until reaching the desired curve angle. Alternatively, the operator first pushes curved supporter 104 distally until reaching the desired curve angle, and then pushes weak straight supporter 102. Finally, the operator pushes distally only weak straight supporter 102 (i.e., while holding both strong straight supporter 106 and curved supporter 104 in place) until accessing the sinus or until reaching the required location within the sinus.

It is noted that as the curved supporter conforms to the straight shape of the strong supporter when both are overlapping, the access system exhibits substantially no bulges or protrusions during insertion into the nasal cavity. Only when the access system is positioned in the desired location near the paranasal sinuses, the curved supporter is extended from the strong supporter and the access system forms a bending path. Thus, the damage to the tissues surrounding the access system on the way to the sinus cavity is reduced as the access system maintains a small cross section with no protrusions or bulges.

In accordance with another embodiment of the disclosed technique, an access system can include several curved supporters each has a different radius of curvature. For example, an access system kit includes several access systems, each having curved supporter of different curvature, such that the operator can choose the access system curvature which best fits the anatomy of the patient. Alternatively, the access system kit includes several curved supporters that can be coupled with the other supporters of the access system (i.e., the strong and the weak supporters). Additionally, the operator can couple several curved supporters for forming together a single continuous curved supporter having several sections of different curvatures. Thereby, the operator can determine the radius of curvature of the curved supporter, and thus the radius of curvature of the access system. Thereby, the operator can adjust the radius of curvature of the access system to the anatomy of the patient.

In accordance with a further embodiment of the disclosed technique, the radius of curvature of the curved supporter can vary along the length of the curved supporter. For example, the radius of curvature can be very small at the distal end of the curved supporter such that even when a short section thereof extends beyond the strong supporter, the curvature angle of the access system is large. That is, the first few millimeters from the distal end of the curved supporter have a very small radius of curvature, while the rest of the curved supporter has a longer radius of curvature.

As mentioned above, the three supporters can be coupled either directly or indirectly. Detailed herein below are some examples of configurations of the three supporters of the access system. Reference is now made to FIGS. 2A-2F, which are schematic illustrations of different concentric configurations of a system, generally referenced 150, for accessing a paranasal sinus cavity of a patient, constructed and operative in accordance with another embodiment of the disclosed technique. Paranasal sinus access system 150 (herein access system 150) is comprised of three concentric tubes: an external tube, a middle tube, and an internal tube. The three tubes have different characteristics in terms of their rigidity and shape memory (i.e., similarly to the supporters of FIGS. 1A-1D). In particular, one of the tubes serves as a straight semi-rigid tube (i.e., weak straight tube), another tube serves as a curved semi-rigid tube (i.e., curved tube), and the third tube serves as a straight rigid tube (i.e., strong straight tube).

In all of the configurations presented in FIGS. 2A-2F, a tube 152 is straight and is semi-rigid (i.e., similarly to weak straight supporter 102 of FIGS. 1A-1D). That is, tube 152 is straight and regains its straight shape when not constrained. The rigidity of tube 152 is the lowest of the three tubes. A tube 154 is curved and is semi-rigid (i.e., similarly to curved semi-rigid supporter 104 of FIGS. 1A-1D). Tube 154 is curved and regains its curved shape when not constrained. The rigidity of tube 154 is higher than that of weak straight tube 152. A tube 156 is straight and is rigid (i.e., similarly to strong straight supporter 106 of FIGS. 1A-1D). The rigidity of tube 156 is the highest of the three tubes.

Figure 2A:
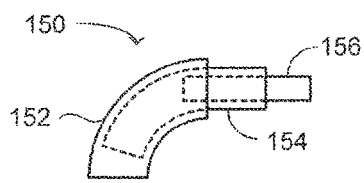
FIGS. 2A-2F are schematic illustrations of different concentric configurations of a system, for accessing a paranasal sinus cavity of a patient, constructed and operative in accordance with another embodiment of the disclosed technique.

With reference to FIG. 2A, access system 150 includes a weak straight external tube 152, a curved middle tube 154, and a strong straight internal tube 156. Internal tube 156 slidably passes via middle tube 154, which in turn slidably passes via external tube 152. It is noted that, in the example set forth in FIGS. 2A-2F the distal direction is toward the left hand side of the Figure.

Access system 150 provides a route (i.e., a work channel) through which at least one tool (not shown) can reach areas within the paranasal sinus of a patient. In other words, the work channel is defined as a passage within access system 150 for enabling a work tool to access to the sinus cavity. The work channel can be a dedicated passage, such as a dedicated lumen within a multilumen sheath enfolding access system 150. The work channel can be incorporated into one of the supporters. For example, the lumen of strong supporter 156 of FIG. 2A is defined as the work channel of access system 150. Alternatively, the work channel can be defined as the lumen within the weak supporter. Once the access system accesses the sinus cavity, the strong and the curved supporters of the access system are retracted, and the lumen of the remaining weak supporter functions as the work channel. The work channel can be embodied as an external sleeve or sheath enfolding the access system. Once the access system enters the sinus cavity, the supporters of the access system are refracted, and the remaining enfolding sheath functions as the work channel. The work channel can be embodied as the intra-volume between the external sheath and the supporters, or the outer most supporter.

It is noted that the tube shaped supporters of FIGS. 2A-2F are merely examples, and as would be detailed further herein below, the supporters can assume any elongated shape, whether tubular or non-tubular, and have any cross-section (e.g., circular, oval, rectangular, hexagonal and the like). Thus, for example, the work channel can pass via any supporter having a lumen running therein regardless of the cross-section of the supporter. Similarly, every feature of the disclosed technique that is described herein with reference to tubular supporters, can also be employed in case of other supporters as well.

The work tool is employed for performing an action within the accessed paranasal sinus. The at least one tool can be for example, a camera, one or more optical fibers, one or more optical bundles, a swab for collecting tissue samples, a suction tube for draining the accessed paranasal sinus, an irrigation tube or an injecting tube for injecting fluids for cleaning the sinus (e.g., saline water) or for injecting other fluids into the sinus (e.g., localized drug delivery), a surgery tool for performing surgical operation in the sinus, a balloon for dilating the ostium of a sinus or opening a sinus blockage, a diagnostic tool such as an ultrasound or an infrared imaging device, a probe, a sensor, a stylet, a guide wire, and the like. Alternatively, the tool (e.g., a swab) is coupled with external tube 152. Further alternatively, the joint lumen of 152, 154 and 156 constitutes a tube through which fluids can be passed into the sinus, obviating the need for a dedicated tube to be inserted therethrough.

It is noted that the access system thus provides access into the sinus cavity for at least one working tool via the work channel. By enabling all required tools to access the sinus cavity through a single access system, the operator can operate the access system and the working tools with only a single hand (i.e., single handed operation). For example, instead of maneuvering a first device (e.g., a camera endoscope) into the sinus cavity with a first hand, and maneuvering a second separate device (e.g., a tissue sampling tool) into the sinus cavity with the other hand, the operator of the access system of the disclosed technique, guides the access system into the sinus cavity single handedly, and once within can operate a tissue sampling tool while viewing the images acquired by a camera fixed to the distal end of the access system.

The route of access system 150 includes a turn or a curve in order to bypass physical obstacles (i.e., due to anatomy of the nasal cavity and paranasal sinuses). The position of the curve along the route of access system 150 and the angle of the curve (i.e., curve angle) are controlled by the operator of access system 150. As mentioned above with reference to FIGS. 1B-1D, the angle of the curve (i.e., also referred to as a bend) is determined by the relative positions of strong straight tube 156 and curved semi-rigid tube 154, and by the radius of curvature of curved semi-rigid tube 154. In particular, the further that curved tube 154 extends beyond strong straight tube 156, the larger the angle of the curve. Once the operator of access system 150 sets the angle of the curve, the operator pushes weak straight tube 152 further distally in the set direction towards a selected area within the paranasal sinus of the patient. The operator can than push the tool via the work channel created by the lumens inside tubes 152, 154 and 156 towards the selected area.

Figure 2B:
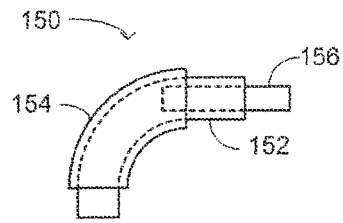
Figure 2C:
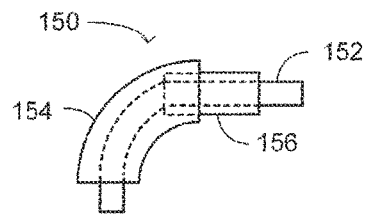
Figure 2D:
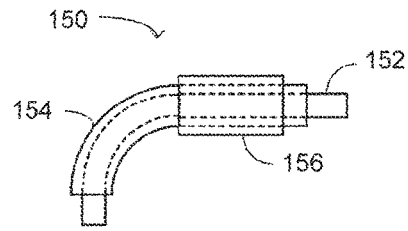
Figure 2E:
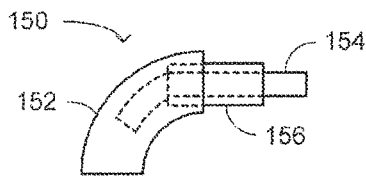
Figure 2F:
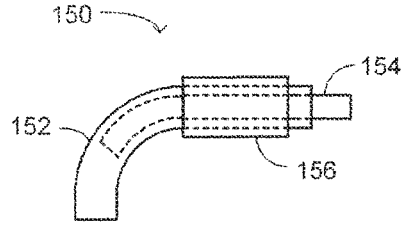
Figure 2G:
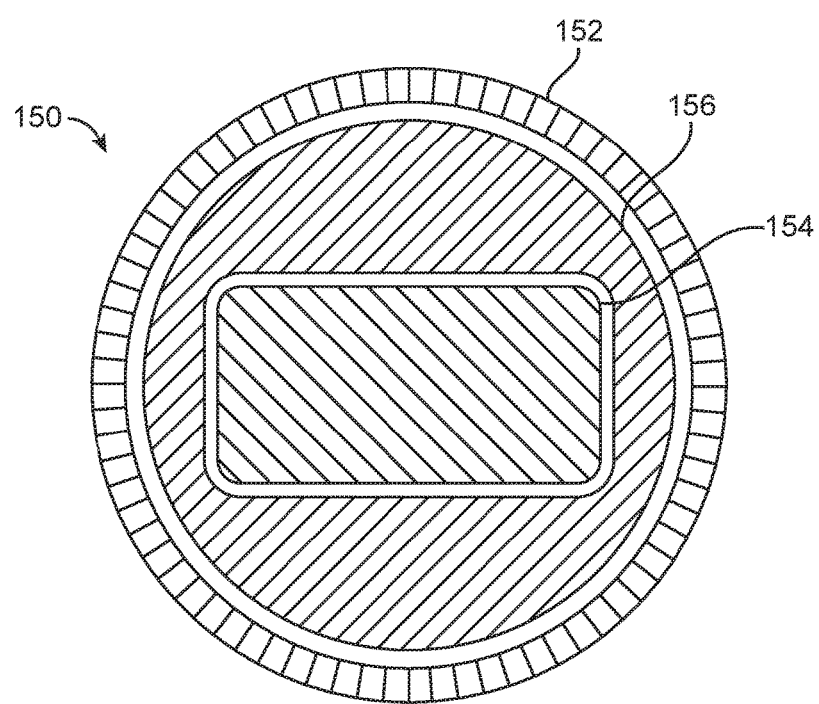
FIG. 2G is a cross-sectional illustration of the embodiment depicted in FIG. 2E.

In the configuration of FIG. 2B, external tube 154 is the curved semi-rigid tube, middle tube 152 is the weak straight tube, and internal tube 156 is the strong straight tube. In the configuration of FIG. 2C, external tube 154 is the curved semi-rigid tube, middle tube 156 is the strong straight tube, and internal tube 152 is the weak straight tube. In the configuration of FIG. 2D, external tube 156 is the strong straight tube, middle tube 154 is the curved tube, and internal tube 152 is the weak straight tube. In the configuration of FIG. 2E, external tube 152 is the weak straight tube, middle tube 156 is the strong straight tube, and internal tube 154 is the curved tube. As mentioned above, the cross-sections of any embodiment of the access system 150 may have any shapes. FIG. 2G shows the cross-sectional shapes of the embodiment of FIG. 2E, in which the external tube 152 has a circular cross section, the middle tube 156 has an outer circular cross section and at least part of the internal tube 154 has a rectangular cross section. The middle tube 156 also includes a recess with a rectangular cross section to allow at least part of the internal tube 154 to pass through. In the configuration of FIG. 2F, external tube 156 is the strong straight tube, middle tube 152 is the weak straight tube, and internal tube 154 is the curved tube.

Figure 3A:
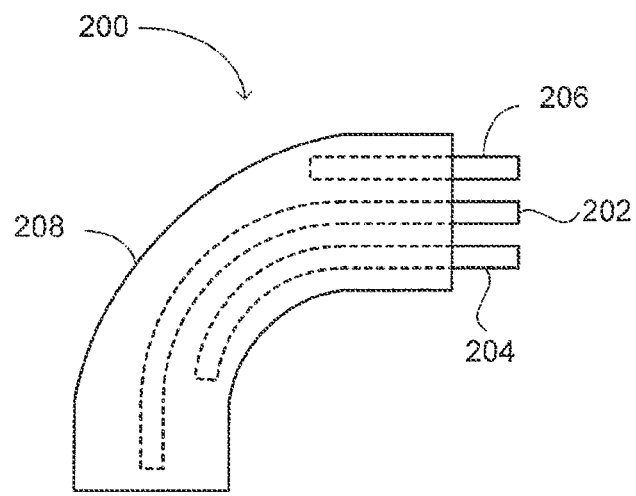
FIGS. 3A and 3B are schematic illustrations of different co-linear configurations of a system, for accessing a paranasal sinus cavity of a patient, constructed and operative in accordance with a further embodiment of the disclosed technique.
Figure 3B:
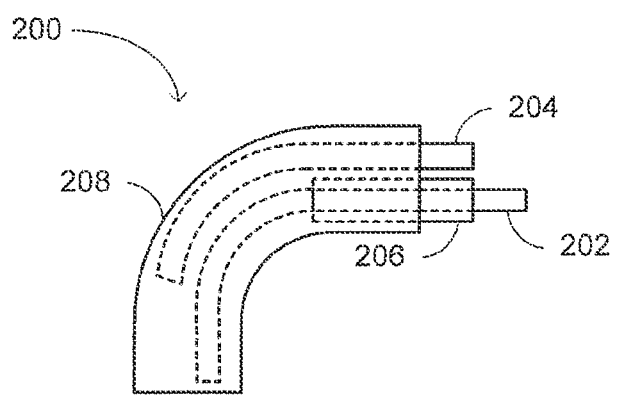

Reference is now made to FIGS. 3A and 3B which are schematic illustrations of different co-linear configurations of a system, generally referenced 200, for accessing a paranasal sinus of a patient, constructed and operative in accordance with a further embodiment of the disclosed technique. Paranasal sinus access system 200 (herein, access system 200) includes an external sheath 208, a straight semi-rigid supporter 202 (i.e., weak straight supporter 202), a curved semi-rigid supporter 204, and a straight rigid supporter 206 (i.e., a strong straight supporter 206). The three supporters pass slidably within external sheath 208 alongside each other (i.e., the supporters are co-linear). External sheath 208 mechanically couples supporters 202, 204 and 206. For example, external sheath 208 couples curved supporter 204 to strong straight supporter 106, such that when they overlap, curved supporter 104 conforms to the straight shape of strong straight supporter 106.

As in previous embodiments, the path (i.e., route) followed by access system 200 during insertion into the paranasal sinus includes a curve (i.e., a bend), which position and angle are controllable by an operator of access system 200. In a similar manner to access system 100 of FIGS. 1A-1D, the curve angle is set by the distance by which the distal end of curved semi-rigid supporter 204 extends beyond the distal end of straight rigid supporter 206 (i.e., strong straight supporter).

External sheath 208 enfolds supporters 202, 204 and 206, and is made of a sealed material. Thereby, sheath 208 prevents contact between the supporters and the tissues of the patient. It is therefore not necessary to disinfect or to sterilize the supporters (and other tools and components which may reside within external sheath 208), for example, when being used among different patients. External sheath 208, which comes into direct contact with the tissues of the patient (e.g., nasal cavity and paranasal sinus) during use, is disposable. That is, external sheath 208 is a single use disposable element designed to enable the other components of access system 200 to be re-used for another patient by simply replacing external sheath 208. Alternatively, external sheath 208 is made from an easily disinfected or sterilizable material, and can be disinfected or sterilized when being used among different patients. Further alternatively, an additional single use elastic sheath may enfold 208. In addition, external sheath 208 is formed of a flexible material. Thereby, sheath 208 when extended distally beyond weak supporter 202 functions as an atraumatic tip for gentle probing of sensitive anatomies.

Each of weak straight supporter 202, curved semi-rigid supporter 204, and strong straight supporter 206 can be bar shaped or tube shaped. The cross section of each of the supporters can be any closed shape, such as a circle, a rectangle, an ellipse and the like. In the case where two supporters or more are constructed as tubes they can be either concentric or run in parallel to each other.

With reference to FIG. 3A, weak straight supporter 202, curved supporter 204 and strong straight supporter 206 are collinear and are sliding along each other. With reference to FIG. 3B, weak straight supporter 202 and strong straight supporter 206 are tube shaped. Weak straight supporter 202 slides within strong straight supporter 206 (i.e., weak supporter 202 and strong supporter 206 are concentric). Curved supporter 204 is co-linear to weak straight supporter 202 and strong straight supporter 206 and slides alongside both. Alternatively, any couple of the supporters can be tube shaped and concentric while the third slides alongside both.

In accordance with another embodiment of the disclosed technique, external sheath 208 can replace weak supporter 202 (i.e., such that weak supporter 202 is omitted from the access system). Thereby, external sheath functions as both the weak supporter and the external sheath isolating the access system from the surrounding tissues. It is noted that the work channel of access system 200 can be defined as a lumen or a passage within external sheath 208.

Reference is now made to FIGS. 4A-4F. FIGS. 4A-4C are schematic illustrations of a system, generally referenced 250, for accessing a paranasal sinus of a patient, constructed and operative in accordance with yet another embodiment of the disclosed technique. FIGS. 4D-4F are schematic illustrations of the access system of FIGS. 4A-4C, in which the external sheath is removed from the image such that the internal portions of the access system are exposed to the viewer for better clarifying the operation thereof.

Access system 250 includes an external sheath 258, a straight semi-rigid supporter 252 (i.e., weak straight supporter 252), a curved semi-rigid supporter 254, and a straight rigid supporter 256 (i.e., strong straight supporter 256). Each of weak straight supporter 252, curved supporter 254 and strong straight supporter 256 is similar in terms of rigidity and shape memory properties to each of weak straight supporter 102, curved supporter 104 and strong straight supporter 106 of FIGS. 1A-1D, respectively. Weak straight supporter 252 is tube-shaped, curved supporter 254 and strong straight supporter 256 are both bar shaped. The supporters are co-linear.

It is notes that dimensions of an entry to a healthy sinus cavity are about 2 mm. Therefore, the maximal outer diameter of access system 250 is about 2.5 mm, and preferably a bit less, for example, 2.2 mm-2.4 mm for preventing (or at least reducing) damage to the patient, pain and inconvenience.

With reference to FIG. 4A, access system 250 is depicted in an initial configuration thereof, in which both strong straight supporter 256 and curved supporter 254 are fully overlapping. In the initial configuration, strong straight supporter 256 forces curved supporter 254 to conform to the straight shape of strong straight supporter 256. The dotted lines in FIG. 4A indicate the distal tip of supporters 252, 254, and 256. Alternatively, the distal tip of each or some of the supporters is positioned proximally to the distal tip of sheath 258. Further alternatively, the distal tip of sheath 258 is occupied by a functional distal head, as detailed further herein below with reference to FIG. 5.

With reference to FIG. 4D, access system 250 is depicted with external sheath 258 being removed from the image, for exposing supporters 252, 254, and 256 to the viewer. As mentioned herein above with reference to FIG. 4A, and as can be seen in FIG. 4D, both curved supporter 254 and weak supporter 252, when overlapping strong straight supporter 256, conform to the straight shape of strong straight supporter 256.

With reference to FIGS. 4B and 4E, an operator of access system 250 pushes curved supporter 254 and weak straight supporter 252 in the distal direction (i.e., in the example set forth in FIGS. 4A-4F the distal direction is toward the left hand side of the Figure). Thereby, the overlap between strong straight supporter 256 and curved supporter 254 becomes smaller, or even vanishes (i.e., depending on the distance by which curved supporter 254 and weak straight supporter 252 are pushed by the operator). A portion of curved supporter 254 which is not overlapping strong straight supporter 256 regains its curved shape and forces a corresponding portion of weak straight supporter 252, to conform to the curved shape of curved supporter 254. Alternatively, the operator pulls strong straight supporter 256 proximally for achieving the same effect and exposing at least a portion of curved supporter 254 from overlapping strong straight supporter 256.

It is noted that, shape memory materials can regain their original shape after being constrained to a different shape. However, the shape memory is not unlimited, and an element made of shape memory material which is highly deformed, may not fully regain its original shape. Curved semi-rigid supporter 254 is straightened by strong straight supporter 256 when they are overlapping each other, and is thereby deformed from its original curved shape. For minimizing the deformation of curved supporter 254, curved supporter 254 is positioned furthest away from the direction of curve of access system 250 (i.e., at the extrados of the curved path of access system). As can be seen in FIGS. 4B and 4E, curved supporter 254 is positioned off-center within sheath 258. In particular, curved supporter 254 is positioned furthest away from the direction of curve of sheath 258 (i.e., and access system 250), thereby its radius of curvature is bigger than if it would have been concentric with sheath 258. Thus, by positioning curved supporter 254 off-center and away from the curve direction, the radius of curvature of curved supporter 254 is increased, for the same radius of curvature of sheath 258. The larger the radius of curvature of curved supporter 254 the less it is being deformed when straightened by strong straight supporter 256.

With reference to FIGS. 4C and 4F, the operator of access system 250 further pushes weak straight supporter 252 distally of both strong straight supporter 256 and curved supporter 254. Thereby, weak straight supporter 252 regains its straight shape. In the final configuration of access system 250, as depicted in FIGS. 4C and 4F, a proximal section of external sheath 258 (i.e., and accordingly of access system 250) is substantially in a straight shape. A middle section of external sheath 258, which is occupied by a portion of curved supporter 254 that is not overlapping strong straight supporter 256, is in a curved shape. The section of external sheath 258 which is occupied by the portion of curved supporter 254 that is not overlapped by strong supporter 256, is termed herein below as the "curved supported section" of external sheath 258. A distal section of external sheath 258, which is occupied solely by weak straight supporter 252 is in a straight shape. It is noted that the operator can further push distally only external sheath 258 which is floppy and functions as an atraumatic tip.

The length of each section of access system 250 is determined by the lengths of each of supporters 252, 254 and 256, and by their relative overlap, as determined by the distance each is pushed by the operator. The curve angle of access system 250 is determined by the radius of curvature of curved supporter 254, and by the length thereof that is not overlapping strong straight supporter 256.

Alternatively, weak straight supporter 252 is in the shape of an external sheath enfolding both curved supporter 254 and strong straight supporter 256. In this manner, access system 250 includes only three elements, however the weak straight external sheath has to be disposed of, disinfected or sterilized, when being used among different patients.

By enfolding access system 250 with external sheath 258, the outer diameter of access system 250 is kept constant or at least continuous (i.e., the outer diameter does not change abruptly or forms a step). The continuous outer diameter stands in contrast to telescopic systems, which diameter differs for different sections thereof. The continuous external diameter reduces damage to the tissues surrounding the access system on the way to the sinus, and within the sinus itself. In some embodiment of the disclosed technique, the weak supporter enfolds the other supporters and other components of the access system, thereby functioning as an external sheath or sleeve. In this case, the outer diameter of the enfolding weak supporter is continuous for reducing the damage to the surrounding tissues.

In accordance with another embodiment of the disclosed technique, the access system further includes a locking mechanism (not shown), for locking all supporters together (e.g., straight weak supporter, curved supporter and straight strong supporter). In other words, the locking mechanism prevents relative movement between the supporters. Alternatively, the locking mechanism only locks two of the supporters together. For example, the locking mechanism locks the strong straight supporter to the curved supporter such that relative movement is disabled (i.e., when moving one of the supporters, the other supporter is also moved in the same way). The locking mechanism is implemented, for example, by a wire coupled to both the distal end and the proximal end of the access system (i.e., or the housing). In the unlocked mode, the wire is untight (i.e., flabby), while in the locked mode the wire is stretched so that the supporters are fixed together and cannot be separately moved. Alternatively, other locking mechanisms can be employed, such as a locking sleeve, a locking component which changes its shape or rigidity when energy (e.g., thermal or electrical energy) or when pressure is applied thereto.

The locking mechanism can be either locked, such that the supporters are bound together, or unlocked such that each supporter can be moved separately. During insertion, or extraction, of the access system into, or out of, the paranasal sinus, the locking mechanism is unlocked. That is, relative movement between the supporters is enabled. It is noted that even when the locking mechanism is locked, the operator can further push or pull the supporters of the access system together (i.e., with substantially no relative movement between the supporters). When the distal tip of the access system is in the required position (e.g., at the desired location within the sinus cavity), the locking mechanism is locked, and relative movement between the supporters is disabled. Thus, for example, the access system is maintained in place while the operator retracts the system or carries out an operation (e.g., using a swab). In accordance with another example, the locking mechanism is locked prior to insertion of the access system to the body of the patient, until the strong straight supporter is properly positioned in the vicinity of the paranasal sinus. Thereafter, the locking mechanism is released (i.e., unlocked), for allowing the strong supporter to be retracted, or the curved supporter to be further advanced. In accordance with a further embodiment of the disclosed technique, the shape of the external sheath can be made tapering (e.g., conical) such that the cross section of the distal end thereof is smaller than the cross section of the proximal end thereof. Thereby, initial insertion of the access system is easier. Additionally, the tapering external sheath gradually dilates the anatomical path to the paranasal sinus and the paranasal sinus itself. Alternatively, in case the access system does not include an external sheath, the access system housing, or otherwise the external-most component of the access system, is tapering. For example, in case the weak supporter enfolds both the strong and the curved supporter, the weak supporter is tapering.

In accordance with yet another embodiment of the disclosed technique, rotary or incremental encoders, or other sensors, are installed between the supporters of the access system for monitoring the relative movement between the supporters. Thereby, the position of the distal end of the access system is determined. Alternatively, the movements of the operating mechanism (not shown—e.g., levers and handles) the operator employs for operating the access system are monitored for determining the location of the distal end of the access system. Further alternatively, motion sensors (e.g., accelerometers and gyroscopes), or position detectors (e.g., ultrasonic or electromagnetic) are installed on, or in the vicinity of, the distal head of the access system for determining the position and orientation of the distal head of the access system.

It is noted that the access system of the disclosed technique enables the operator to reach more than one sinus cavity (e.g., maxillary and frontal) with the same access system, and without retracting the system from the patient's body. For example, while the strong supporter is maintained within the patient's nose, the operator can maneuver the access system among the different sinus cavities. Accessing two or more sinus cavities without fully retracting the access system saves time and effort to the operator, and reduces the inconvenience of the patient.

Figure 5:
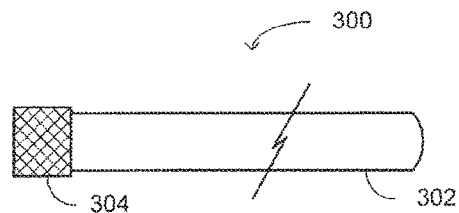
FIG. 5, which is a schematic illustration of an external sheath, of a paranasal sinus access system, constructed and operative in accordance with yet a further embodiment of the disclosed technique.

Reference is now made to FIG. 5, which is a schematic illustration of an external sheath, generally referenced 300, of a paranasal sinus access system, constructed and operative in accordance with yet a further embodiment of the disclosed technique. External sheath 300 includes a sheath body 302 and a functional distal head 304. External sheath 300 enfolds there-within a sinus access system (e.g., access system 250 of FIGS. 4A-4F) which is employed for accessing a paranasal sinus of a patient. It is noted that after insertion into the sinus cavity, the access system can be withdrawn from the body of the patient while external sheath 300 remains therein, for providing access therethrough to at least one tool into the sinus.

In the example set forth in FIG. 5, functional distal head 304 is a swab head 304. Swab head 304 is directed at acquiring a tissue sample or other sample from within the paranasal sinus of the patient. The operator rubs swab head 304 against the inner tissue of the sinus for acquiring tissue sample. Alternatively, functional distal head can include other tools for performing other actions within the sinus of the patient, such as a dilation balloon, a camera, a heat source, a laser source, a light source, drainage nozzle, irrigation nozzle, injection element, and the like.

In accordance with another embodiment of the disclosed technique, the functional distal head of the system is rotatable (not shown). The rotatable head can be moved (e.g., rotated) separately from the supporters of the access system. Thereby, the rotatable functional distal head provides at least one additional degree of freedom to the access system. The movement of the rotatable head can be controlled, for example, by employing wires, applying thermal energy to shape memory materials or by other actuating mechanisms.

Once the access system is properly positioned within the sinus of the patient, the access system can be secured in place (e.g., by employing a locking mechanism or a balloon), such that only the functional distal head 304 can be rotated (i.e., or otherwise moved). When the rotatable head is also properly positioned at the desired location and orientation, it can be secured in place as well, and the operator can operate the functional element of the rotatable function distal head. It is noted that once the access system and the rotatable head are secured in place, at least some of the supporters can be refracted from the body of the patient.

For example, the rotatable functional distal head can include optical sensors and other optical components (e.g., lenses, prisms and mirrors) for enabling the operator to view (i.e., or to image) the interior volume of paranasal cavity. The rotatable head including the optical sensors can be rotated to enable the operator to examine different portions of the paranasal cavity.

In accordance with a further embodiment of the disclosed technique, the functional distal head includes at least one port (not shown). For example, the port can be configured as a port for transfer of fluids (e.g., gas or liquid) into or out of the sinus cavity (i.e., fluids port). The fluids port is coupled with a fluid passageway through which the fluids pass. For instance, in case the weak supporter is tubular, its lumen can serve as the fluids passageway. Alternatively, the work channel of the access system can include, or can serve as, the fluid passageway.

The fluid port can be formed as an opening in the functional distal head enabling fluids passage through the distal head. The fluid passageway can be formed by a single channel (i.e., conduit), or a network of channels. The distal end of the fluid passageway (i.e., located out of the body of the patient) is connected to a fluid container and possibly to a fluid pumping mechanism (e.g., a syringe or a pump), for pumping the fluid through the fluid passageway into or out of the sinus cavity. The fluids can be, for example, saline, biological agents, chemical agents, drugs, antibiotics, and the like. The fluids can be employed for irrigation, cleaning other components installed on the functional head (e.g., optical components such as a camera or illumination components such as a fiber bundle).

The fluid port, or the fluid passageway, can include a valve for regulating fluid passage therethrough. For example, the valve can be employed for switching fluid passage modes, such as switching between an irrigation mode, in which fluids are irrigating the sinus cavity, and between camera cleaning mode, in which fluids are directed toward the camera for cleaning it. The valve can be controlled by the fluid pressure or by another remote control mechanism, such as a pull wire, applying electrical energy to a piezoelectric element, and the like. It is noted that the fluids pumped into the sinus cavity can be employed for collecting intracavitary tissue, mucous and liquids samples by flooding the sinus cavity (e.g., with saline), collecting the flooding fluid, and filtering tissue, mucous and liquids samples therefrom.

The functional head can include several ports that can either be identical or different than each other. The ports can be formed and employed for different applications. The different ports can be coupled with separate fluid channels, containers and pumping mechanisms. It is noted that the ports of the functional head can further include therapeutic or diagnostic probes (e.g., a laser source, an IR source, an ultrasound source). The ports can also include sensors, such as position sensors, velocity sensors, acceleration sensors, temperature sensors, pressure sensors, biological sensors, chemical sensors, force sensors, electro-optical sensors, and the like. For example, each image acquired by a camera installed on the functional head is associated with readings from a magnetic position sensor mounted on the head.

In accordance with yet another embodiment of the disclosed technique, the functional distal head of the access system is displaceable with respect to the access system. For example, the distal head is coupled to sheath body 302 (or to the weak supporter—not shown) via a hinge. In this manner, the functional distal head can switch between a first position in which it seals the distal end of sheath body 302, and a second position in which the distal end of sheath body is open. For instance, when the operator pushes the access system into the body cavity, the distal head that includes a camera provides a frontal view of the passed through anatomy to the operator. Once the operator reaches the required location within the body cavity, the distal head is opened, thereby, enabling the operator to transfer a working tool via the body sheath.

Furthermore, the displaceable distal head may include back-to-back arrangement. In other words, a first side of the distal head includes a camera, and the other side includes a tissue sampling tool (e.g., a swab). Thus, the operator employs the camera for accessing the sinus cavity, and once positioned there-within, the operator switches the sides of the functional head, and can employ the swab for sampling intracavitary tissue, mucous and liquids. Alternatively, the back-to-back arrangement includes a first camera (and/or illumination) in a first side of the distal head, and a second camera (and/or illumination) in the other side. Thus, the operator employs the first camera for accessing the sinus cavity, and once positioned there-within, the operator switches the sides of the functional head, and can employ the second camera while simultaneously employing a working tool within the sinus cavity.

In the examples set forth herein above with reference to FIG. 5, the functional distal head is coupled at the distal end of an external sheath. Alternatively, the functional distal head is coupled with the distal most element of the access system. For example, in case the weak supporter enfolds the other supporters of the access system and functions as the external sheath, the functional distal head is coupled at the distal end of the weak supporter.

Figure 6A:
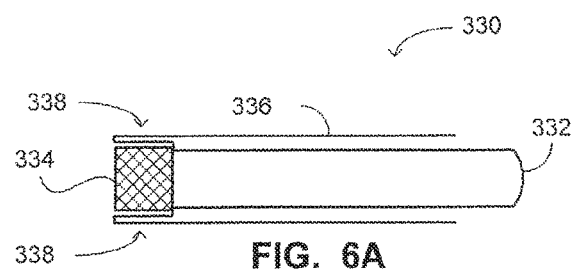
FIGS. 6A and 6B are schematic illustrations of a system for accessing a paranasal sinus cavity of a patient, constructed and operative in accordance with yet another embodiment of the disclosed technique.
Figure 6B:
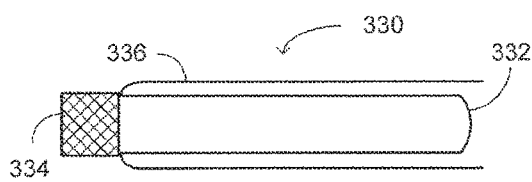

Reference is now made to FIGS. 6A and 6B, which are schematic illustrations of an external sheath, generally referenced 330, of a paranasal sinus access system constructed and operative in accordance with yet another embodiment of the disclosed technique. External sheath 330 includes a sheath body 332, a swab head 334, and a foldable sleeve 336. Foldable sleeve 336 includes an unstitched hem 338. Foldable sleeve 336 enfolds sheath body 332 and swab head 334. In particular, foldable sleeve 336 is coupled with sheath body 332 proximally to the distal end (not referenced) of swab head 334, such that unstitched hem 338 enfolds swab head 334. Each of sheath body 332 and swab head 334 is substantially similar to sheath body 302 and swab head 304 of FIG. 5, respectively.

Foldable sleeve 336 is sealed and prevents sheath body 332 and swab head 334 from coming into contact with the tissues of the patient during insertion of the access system and external sheath 330 into the paranasal sinus of the patient. It is noted that once swab head 334 is positioned within the sinus cavity, the operator may remove the access system from the body of the patient. When swab head 334 is positioned within the sinus cavity, the operator of the access system pulls foldable sleeve 336 proximally (i.e., in the example set forth in FIGS. 6A and 6B, the proximal direction is to the right hand side of the Figure) such that hem 338 is straightened, and swab head 334 is exposed. The operator rubs swab head 334 against the inner tissue of the sinus for acquiring tissue sample. The operator removes external sheath 330, including the tissue sample within swab head 334 for analyzing the sampled tissue. In this manner, the operator samples only the sinus tissue (i.e., and not other tissues on the way to the sinus tissue), thereby, increasing the accuracy of analysis of the tissue sample.

It is noted that sheath body 332 remains enfolded within sleeve 336 throughout the insertion of access system 330 into the sinus and therefore remains sterile. Therefore, the access system enfolded within external sheath 330 (i.e., in case it is not retracted by the operator) can be re-used for another patient, once sleeve 336 and swab head 334 are replaced (i.e., disposable elements), disinfected or sterilized. It is further noted that sheath body 332 can further include a work channel therewithin. Thus, sheath body 332 can house at least one working tool, such as a camera. The camera can acquire images of the sinus cavity and throughout the insertion of the access system to the sinus. In a similar manner to the access system within sheath body 332, the camera is protected by sleeve 336 and is re-usable as well. Alternatively, sheath body 332 can contain other re-usable working tools, such as an ultra-sound imager, a heat source, or a laser source, as long as the tools are not required to come into contact with the sinus tissues.

Figure 7A:
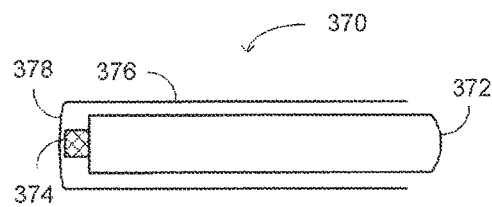
FIGS. 7A and 7B are schematic illustrations of a system for accessing a paranasal sinus cavity of a patient, constructed and operative in accordance with yet a further embodiment of the disclosed technique.
Figure 7B:
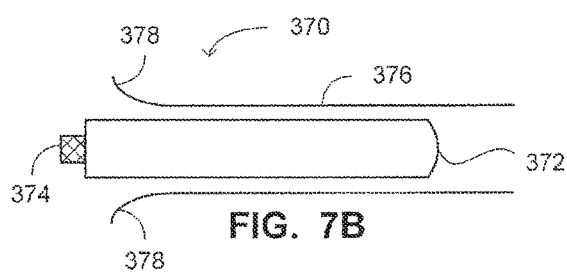

Reference is now made to FIGS. 7A and 7B, which are schematic illustrations of an external sheath, generally referenced 370, of a paranasal sinus access system, constructed and operative in accordance with yet a further embodiment of the disclosed technique. External sheath 370 includes a sheath body 372, a functional distal head 374, and a puncturable sleeve 376. External sheath 370 enfolds a paranasal sinus access system. Additionally, sheath body 372 can enfold other tools, such as a camera, or a laser source. Puncturable sleeve 376 enfolds sheath body 372 and functional distal head 374. Each of sheath body 372 and functional distal head 374 is substantially similar to sheath body 302 and functional distal head 304 of FIG. 5, respectively.

Puncturable sleeve 376 prevents sheath body 372 and functional distal head 374 from coming into contact with the tissues of the patient during insertion of the access system into the paranasal sinus of the patient. When functional distal head 374 is positioned within the sinus cavity, the operator of the access system pulls puncturable sleeve 376 proximally (i.e., in the example set forth in FIGS. 7A and 7B, the proximal direction is to the right hand side of the Figure) such that functional distal head 374 punctures the distal end of puncturable sleeve 376 and is thereby exposed. Alternatively, the operator pushes functional distal head 374 distally to puncture puncturable sleeve 376. The operator employs functional distal head for performing an action within the tissue of the patient, such as inflating a dilation balloon within the ostium of the sinus, acquiring tissue sample from the sinus, ablating tissues of the sinus, irrigating the sinus, draining fluids from the sinus, injecting substances into the sinus (e.g., localized drug delivery), and the like. Sheath 372 can either be re-usable upon disinfection or sterilization, or can be disposable. The access system sealed within the sheath body 372, as well as other working tools which are sealed within sheath body 372 (e.g., a camera) can be re-used for other patients.

Figure 8:
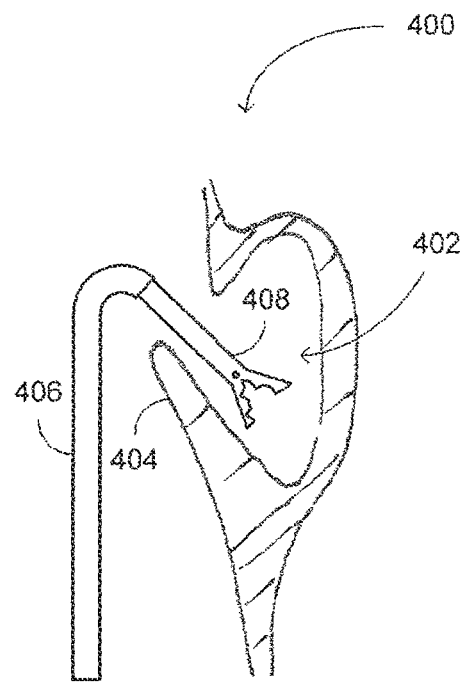
FIG. 8 is a schematic illustration of a paranasal sinus environment, which is accessed by an access system, constructed and operative in accordance with yet another embodiment of the disclosed technique.

Reference is now made to FIG. 8, which is a schematic illustration of a paranasal sinus environment, generally referenced 400, which is accessed by an access system, constructed and operative in accordance with yet another embodiment of the disclosed technique. Sinus environment depicts a paranasal sinus cavity 402, a sinus cavity flap 404 (e.g., the uncinate process), an access system 406 and a working tool 408. Access system 406 is a paranasal sinus access system substantially similar to access system 250 of FIGS. 4A-4F. Access system 406 includes a work channel, through which an operator of access system 406 can insert working tool 408 into sinus cavity 402. Working tool 408 is a working, therapeutic or diagnostic tool for performing an action within cavity sinus 402. For example, working tool 408 can be a camera, a balloon catheter, a washing catheter, a draining catheter, a tissue ablating tool, a grasper, a biopsy collector, and the like.

As can be seen in FIG. 8, for accessing sinus cavity 402, access system 406 (i.e., and in particular the work channel within) have to maneuver around sinus cavity flap 404 and make a turn of an angle exceeding 90 degrees. Such an acute turn in a limited space as that of the anatomy of the nasal cavity and the paranasal sinuses, requires that access system 406 would maneuver to achieve a wide range of curve angles over a very small radius of curvature. In particular, for accessing sinus cavity 402, access system 406 should conform to a radius of curvature of between 2-5 mm, and achieve angles up to 180 degrees.

As mentioned above with reference to FIGS. 4A-4F, shape memory elements regain their original shape after being deformed. However, the shape regaining is not unlimited and an element which is drastically deformed might not fully regain its original shape. With reference to FIGS. 4A-4F, curved supporter 254 is positioned off the center (not shown) of the cross section of sheath 258. In particular, curved supporter 254 is positioned at, or toward, the end of the cross section of sheath 258, which is furthest away from sinus cavity 404. That is, the curved supporter is positioned at, or toward, the extrados of the bend of the access system. Thereby, the radius of curvature of curved supporter 254 is larger than in case curved supporter 254 would have been positioned in the center of the cross section of sheath 258.

Additionally, curved supporter 254 is non-tubular, e.g., a bar shaped. A bar shaped shape memory element may withstand higher deformations than a tube shape element. Furthermore, a tube shaped element when deformed by a curvature may become oblate (i.e., its cross section becomes oval) thereby decreasing its diameter in one axis. Therefore, every element passing through curvedly deformed tube should have a diameter smaller than that of the tube for allowing for the oblation of the tube. For example, the diameter of working tool 408 should be sufficiently smaller than that of the work channel of access system 406, for allowing for the oblation of the work channel when curvedly deformed by the curved semi-rigid supporter.

In accordance with another embodiment of the disclosed technique, the curved supporter is formed by a wire made of shape memory material. The cross section of the wire can be of any shape, such as circular, oval, rectangular, hexagonal, and the like. Alternatively, the curved supporter is formed by more than a single wire. For example, the curved supporter is formed from two or more wires coupled together side by side. For instance, the wires can have a circular cross section, or a rectangular cross section (i.e., thereby forming together a bar shaped curved supporter).

In accordance with a further embodiment of the disclosed technique, the curved supporter is bar shaped and the strong straight supporter is tube shaped. The strong straight supporter includes a distal end configured to enable coupling (e.g., slidable coupling) between the two supporters. The distal end of the straight strong supporter may include a curved supporter recess configured to receive the curved supporter, as depicted, for example, hereinafter in FIGS. 16A-18B. Additionally, the distal end enables the weak supporter to smoothly move (e.g., slide) over the strong supporter and the curved supporter, and in particular, over the end of the strong supporter where the curved supporter is being curved.

Figure 9:
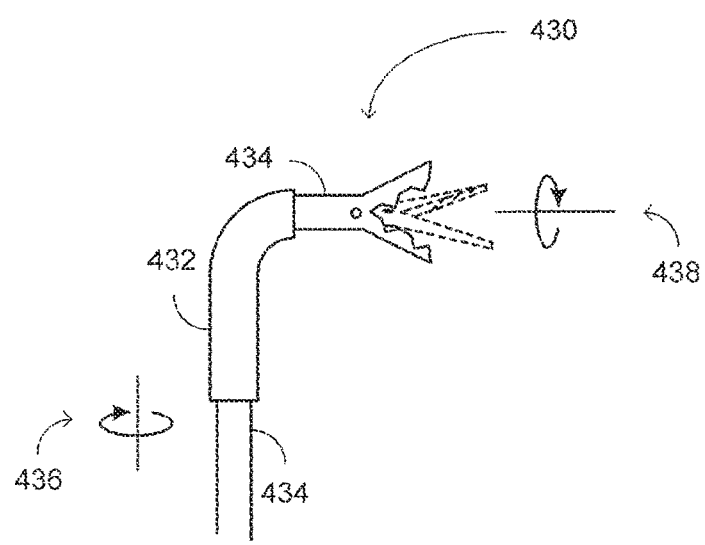
FIG. 9 is a schematic illustration of an access system, constructed and operative in accordance with a yet further embodiment of the disclosed technique.

Reference is now made to FIG. 9, which is a schematic illustration of an access system, generally referenced 430, constructed and operative in accordance with yet a further embodiment of the disclosed technique. Access system 430 includes an external sheath 432 and a working tool 434. Sheath 432 is substantially similar to sheath 402 of FIG. 8, and enfolds therewithin a weak straight supporter, a curved supporter and a strong straight supporter (all not shown). Working tool 434 slidably passes through a work channel (not shown) of sheath 432. As can be seen in FIG. 9, working tool 434 can be rotated around its central axis 438 without rotating sheath 432. In particular, working tool 434 rotates around axis 436 and 438 without moving sheath 432.

Figure 10:
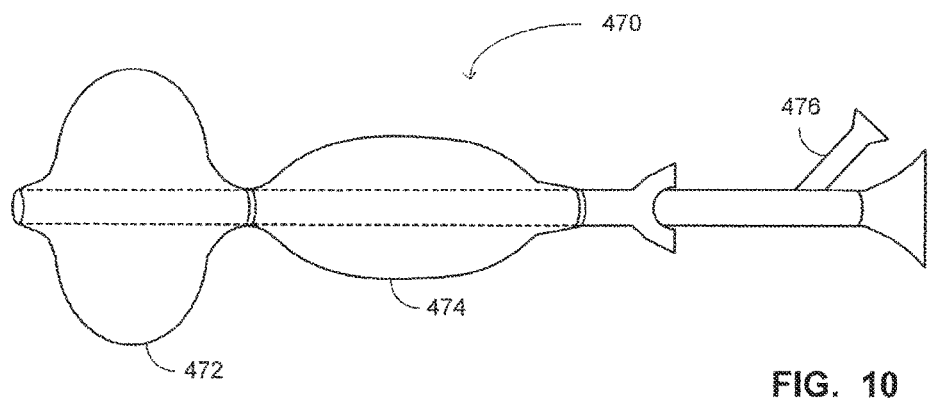
FIG. 10 is a schematic illustration of a balloon dilation catheter, constructed and operative in accordance with yet another embodiment of the disclosed technique.

Reference is now made to FIG. 10, which is a schematic illustration of a balloon dilation catheter, generally referenced 470, constructed and operative in accordance with yet another embodiment of the disclosed technique. Balloon dilation catheter 470 includes a first balloon 472, a second balloon 474, and a fluid channel 476. First balloon 472 and second balloon 474 are in fluid communication with each other. Fluid channel 476 is in fluid communication with both first balloon 472 and second balloon 474 for providing fluid (e.g., saline solution, air) to first and second balloons 472 and 474. Each of first balloon 472 and second balloon 474 can either be a compliant, semi-compliant or non-compliant balloon. In the example set forth in FIG. 10, first balloon 472 is a compliant or semi-compliant balloon, and second balloon 474 is a non-compliant balloon.

An operator of an access system (e.g., access system 250 of FIGS. 4A-4F) employs the access system for accessing a paranasal sinus of a patient. The operator inserts balloon dilation catheter 470 through a work channel of the access system. Alternatively, balloon catheter 470 is detachably mounted over the access system (e.g., similarly to external sheath 300 of FIG. 5).

It is noted that both first balloon 472 and second balloon 474 are deflated during insertion into the sinus cavity. The operator positions first balloon 472 within the sinus cavity of the patient, and positions second balloon 474 within the ostium of the sinus (i.e., the opening to the sinus cavity). The operator inflates both first balloon 472 and second balloon 474, for gradually broadening the ostium (i.e., increasing the diameter thereof). Second balloon 474 is constrained by the ostium and therefore can only inflate to a certain volume. First balloon 472, which is positioned within the sinus cavity, is not constrained and can be inflated to its maximal volume and stretch (i.e., in case of compliant or semi-compliant balloon).

As detailed above, first balloon 472 is in fluid communication with second balloon 474. Therefore, the pressure between balloons 472 and 474 is in equilibrium. Thus, compliant or semi-compliant first balloon 472, serves as a pressure reservoir for non-compliant second balloon 474. As second balloon 474 is pressed against the walls of the ostium of a sinus, any change in the dimensions of the ostium is compensated by a volume change of first balloon 472 for maintaining the pressure equilibrium.

First balloon 472 and second balloon 474 are maintained within the sinus cavity and the ostium of the sinus, respectively, for a period of time determined by the operator (e.g., one hour, one day or one week). It is noted that the operator can remove the access system and balloon catheter 470, while maintaining balloons 472 and 474 in the sinus and ostium. After that period of time has ended, the operator removes both balloons from the sinus and ostium of the patient by re-employing the access system.

In accordance with an alternative embodiment of the disclosed technique, the access system (e.g., access system 250 of FIG. 4A) is coupled with a balloon. The operator of the access system can inflate and deflate the balloon, for example, for dilating sections of the anatomy of the patient on the way to the sinus cavity, or within the sinus cavity itself.

Further alternatively, the access system includes a dilating tube enfolding the access system. The dilating tube can be, for example, a sleeve having a tapering distal end, that enfolds the access system and that can be inflated and deflated by the operator for dilating sections of the anatomy of the patient. The dilating tube is coupled with a fluid channel running along, outside, or within, the access system. The fluid channel enables an inflating fluid (e.g., saline) to be pumped into or out of the dilating tube. The fluid channel is coupled with an inflating fluid reservoir on the proximal end of the access system, outside of the body of the patient. The dilating tube can enfold the entire length of the access system or only a section of the access system (e.g., enfolding the distal end of the access system or enfolding a section which is positioned proximally to the distal end). The operator can employ the dilating tube to dilate sections of the anatomy of the patient within the sinus cavity or on the way to the sinus cavity. Additionally, the operator can employ the dilating tube for anchoring the access system in place by inflating the dilating tube such that it snuggly fits the surrounding anatomy of the patient. Thereby the inflated dilating tube prevents the access system from sliding distally or proximally from its current location.

Figure 11:
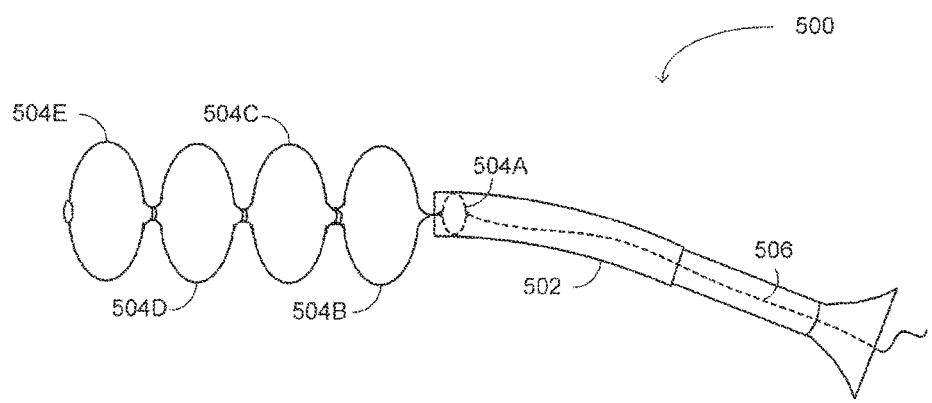
FIG. 11 is a schematic illustration of a balloon dilation catheter, constructed and operative in accordance with yet a further embodiment of the disclosed technique.

Reference is now made to FIG. 11, which is a schematic illustration of a balloon dilation catheter, generally referenced 500, constructed and operative in accordance with yet a further embodiment of the disclosed technique. Balloon dilation catheter 500 includes a balloon holding sleeve 502, a series of balloons 504A, 504B, 504C, 504D, and 504E, and a balloons inflation channel 506. Each of balloons 504A-504E is in fluid communication with adjacent balloons. Balloons inflation channel 506 is in fluid communication with balloons 504A-504E.

An operator inserts balloons 504A-504E into the ostium of a paranasal sinus of a patient by employing an access system (e.g., access system 250 of FIGS. 4A-4F). During insertion, balloons 504A-504E are enfolded by balloon holding sleeve 502, and are deflated. When arriving to the ostium, the operator pulls balloon holding sleeve 502 proximally to expose at least one of balloons 504A-504E. In the example set forth in FIG. 11, the operator exposes four balloons 504B-504E, while maintaining a single balloon 504A enfolded within balloon holding sleeve 502. Thereby, the operator controls the length of the balloon employed in the dilation procedure. It is noted that balloon dilation catheter 500 can include any number of balloon (e.g., two balloons or eight balloons).

Once balloons 504B-504E are positioned within the ostium of a sinus, the operator can remove the access system while maintaining balloons 504A-504E, balloon holding sleeve 502 and balloons inflation channel 506 within the patient. It is noted, however, that the proximal end of balloons inflation channel 506 remains outside of the body of the patient. The operator inflates balloons 504B-504E via balloons inflation channel 506 for applying pressure on the walls of the ostium for increasing the diameter thereof. After a period of time, the operator can deflate balloons 504B-504E, and remove balloons 504A-504E, holding sleeve 502 and balloons inflation channel 506 by employing the access system.

Figure 12A:
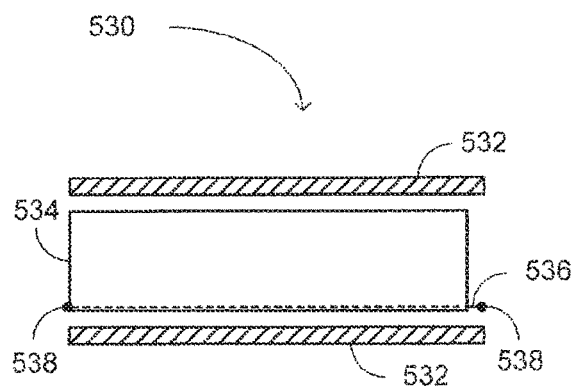
FIGS. 12A-12C are schematic illustrations of a system for accessing a paranasal sinus cavity of a patient, constructed and operative in accordance with yet another embodiment of the disclosed technique.
Figure 12B:
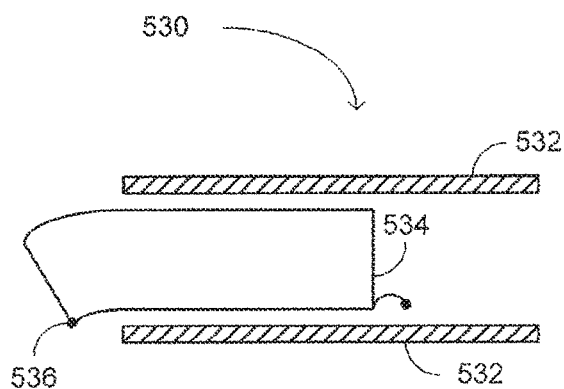
Figure 12C:
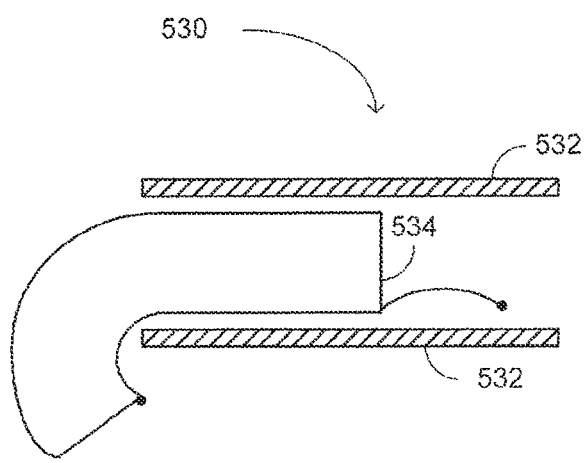

Reference is now made to FIGS. 12A-12C, which are schematic illustrations of a system for accessing a paranasal sinus of a patient generally referenced 530, constructed and operative in accordance with yet another embodiment of the disclosed technique. Access system 530 includes an external sheath 532, an inner curving tube 534, and a pull wire 536. External sheath 532 enfolds inner curving tube 534. Pull wire 536 runs through a dedicated wire channel (not shown) on the perimeter of curving tube 534. Pull wire includes two restrain beads 538 at either end thereof. Sheath 532 is formed of a rigid material. Curving tube 534 is formed of a flexible material which can be flexed upon appliance of pressure. Additionally, system 530 can further include a straight semi-rigid supporter (i.e., a weak straight supporter—not shown), slidably coupled within curving tube 534. Further additionally, a tool can also slide through curving tube 534 along the weak straight supporter.

With reference to FIG. 12A, curving tube 534 is slidably coupled within sheath 532 and is pushed distally (i.e., in the example set forth in FIGS. 12A-12C the distal direction is toward the left hand side of the Figure) by an operator of access system 530. With reference to FIG. 12B, once the operator wants to curve access system 530 around an obstacle (e.g., sinus flap 404 of FIG. 8), the operator pulls wire 536 while pushing curving tube 534 proximally, thereby, curving tube 534 begins to curve. With reference to FIG. 12C, the operator can control the curve angle of curving tube 534 by continuing to push curving tube distally, while pulling wire 536 proximally, until reaching the desired curve angle. It is noted, that the operator can pull wire 536, while curving tube is positioned within sheath 532. Thereby, sheath 532 would constrain curving tube 534 from curving in a similar manner to a strong straight supporter.

Figure 13:
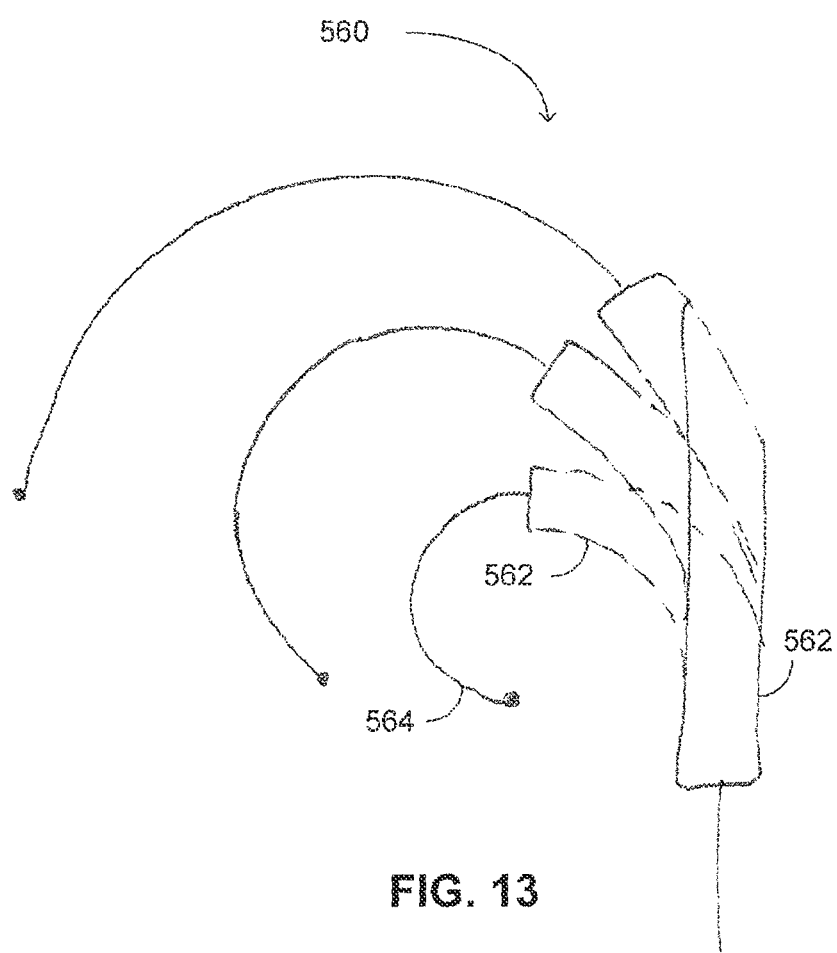
FIG. 13 is a schematic illustration of a curved supporter producer, constructed and operative with yet a further embodiment of the disclosed technique.

Reference is now made to FIG. 13, which is a schematic illustration of a curved supporter producer, generally referenced 560, constructed and operative with yet a further embodiment of the disclosed technique. Curved supporter producer 560 includes a radius shaper 562 and a curved supporter 564. Radius shaper 562 is made of a memory shape material and is curved. Alternatively radius shaper 562 is a steerable sheath (e.g., curving sheath 534 of FIGS. 12A-12C, or other deflection mechanism). Radius shaper (i.e., in case it is made of shape memory material) 562 is more rigid than a weak straight supporter (not shown) and is less rigid than a strong straight supporter, both of an access system (e.g., system 100 of FIGS. 1A-1D). Thus, when radius shaper 562 extends beyond the strong straight supporter, radius shaper 562 regains its original curved shape. In the examples set forth in FIG. 13, three alternative radius shapers 562 are drawn, of varying curvatures. Curved supporter 564 is elongated shaped rigid material exhibiting plastic behavior. An operator of the access system pushes curved supporter 564 through radius shaper 562, and thereby rolls curved supporter 564 at a radius determined by the radius of curvature of radius shaper 562. The operator determines the angle of curve of curved supporter by controlling the length of curved supporter extending through radius shaper 562.

Figure 14A:
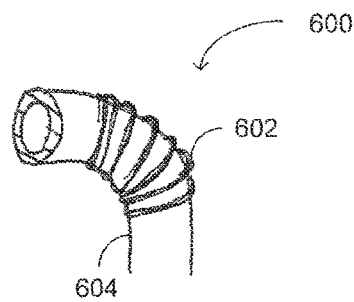
FIG. 14A is a schematic illustration of a curved supporter, constructed and operative with yet another embodiment of the disclosed technique.

Reference is now made to FIG. 14A, which is a schematic illustration of a curved supporter, generally referenced 600, constructed and operative with yet another embodiment of the disclosed technique. Curved supporter 600 includes a shape memory portion 602 and a flexible portion 604. Shape memory portion 602 regains its original shape after being deformed and thereby gives curved supporter 600 its curved shape when not overlapping with a strong straight supporter of an access system. In the example set forth in FIG. 14A, flexible portion 604 is in the shape of a tube, and shape memory portion 602 is in the form of a curved helical wire. Shape memory portion 602 is wound around flexible portion 604.

Figure 14B:
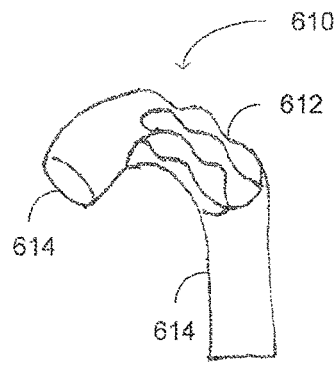
FIG. 14B is a schematic illustration of a curved supporter, constructed and operative with yet a further embodiment of the disclosed technique.

Reference is now made to FIG. 14B, which is a schematic illustration of a curved supporter, generally referenced 610, constructed and operative with yet a further embodiment of the disclosed technique. Curved supporter 610 includes a shape memory portion 612 and a flexible portion 614. In the example set forth in FIG. 14B, flexible portion 614 is in the shape of a tube, and shape memory portion 612 is in the shape of a closed shape cut pattern having a curved shape memory.

Figure 14C:
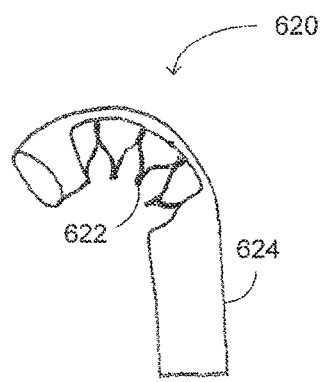
FIG. 14C is a schematic illustration of a curved supporter, constructed and operative with yet another embodiment of the disclosed technique.

Reference is now made to FIG. 14C, which is a schematic illustration of a curved supporter, generally referenced 620, constructed and operative with yet another embodiment of the disclosed technique. Curved supporter 620 includes a shape memory portion 622 and a flexible portion 624. In the example set forth in FIG. 14C, flexible portion 624 is in the shape a tube having a strip-shaped cut pattern, and shape memory portion 622 is in the form of a strip-shaped wire mesh completing the tube shape of (i.e., filling the cut pattern of) flexible portion 614.

Figure 14D:
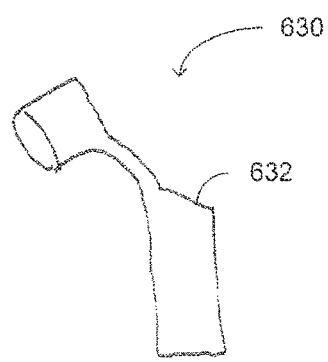
FIG. 14D is a schematic illustration of a curved supporter, constructed and operative with yet a further embodiment of the disclosed technique.

Reference is now made to FIG. 14D, which is a schematic illustration of a curved supporter, generally referenced 630, constructed and operative with yet a further embodiment of the disclosed technique. Curved supporter 630 is made of a shape memory material in is in the form of an incomplete tube.

Figure 15:
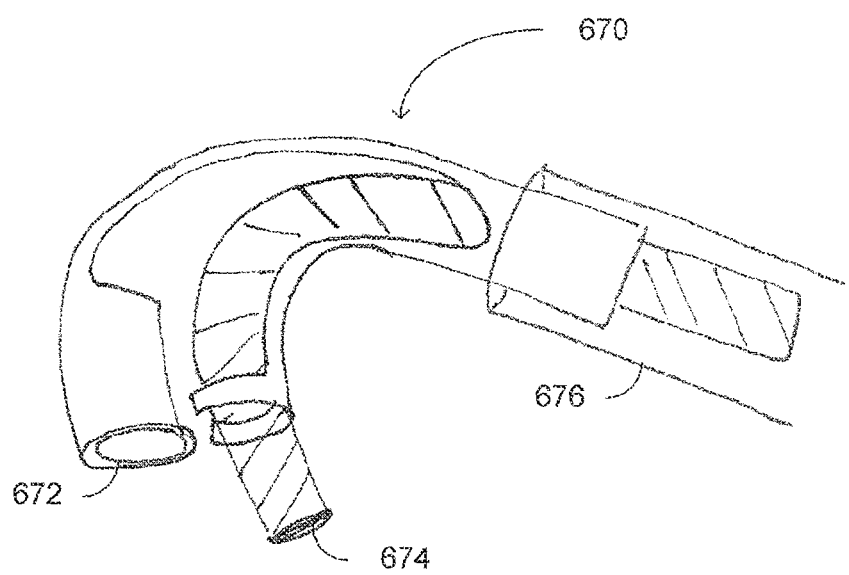
FIG. 15 is a schematic illustration of a split working tool, constructed and operative with yet another embodiment of the disclosed technique.

Reference is now made to FIG. 15, which is a schematic illustration of a split working tool, generally referenced 670, constructed and operative with yet another embodiment of the disclosed technique. Split tool 670 is inserted into the sinus of a patient by employing an access system (e.g., system 250 of FIG. 4A-4D) via lumen 676 of the access system (i.e., lumen 676 defines a work channel of the access system). Split tool includes a bifurcated distal head tool 672 and a bifurcated proximal tool 674. Distal head tool 672 occupies the distal end of split tool 670 and is substantially short (e.g., a camera, a laser source and the like). Proximal tool is positioned proximally to distal head tool 672 (i.e., concentric with distal head tool 672) and can either be short or elongated (e.g., an irrigation or drainage catheter). When split tool 670 extends distally to lumen 676, split tool 670 splits such that both distal head tool 672 and proximal tool 674 and parallel to each other.

Figure 16A:
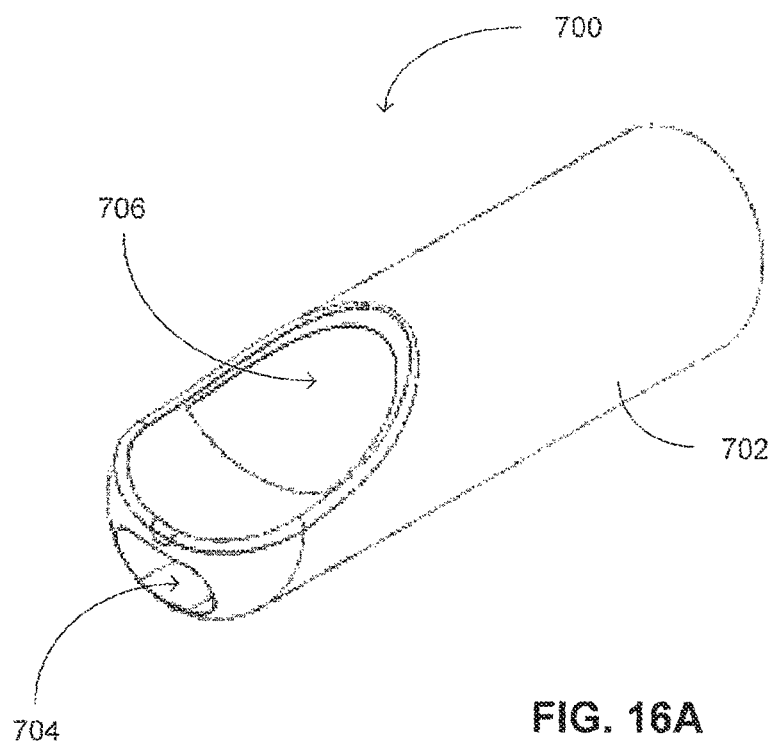
FIGS. 16A and 16B are schematic illustrations of a distal end of a strong straight supporter, constructed and operative with yet a further embodiment of the disclosed technique.
Figure 16B:
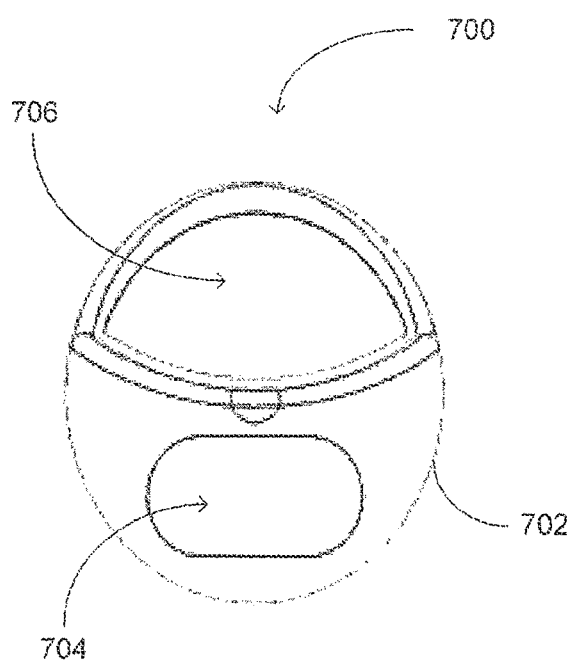

Reference is now made to FIGS. 16A and 16B, which are schematic illustrations of a distal end of a strong straight supporter, generally referenced 700, constructed and operative with yet a further embodiment of the disclosed technique. FIG. 16A depicts the distal end of strong supporter 700 from an isometric perspective. FIG. 16B depicts the distal end of strong supporter 700 from a front view perspective. Strong supporter 700 together with a weak supporter and a curved supporter (both not shown) form together a sinus access system (not shown—e.g., access system 250 of FIG. 4A). Strong supporter 700 includes a distal end 702, a curved supporter recess 704 and a work channel recess 706.

Distal end 702 (or at least its proximal side) of strong supporter 700 has the same cross section as the rest of strong supporter 700 such that strong supporter 700 forms a continuous elongated body. As can be seen, for example, in FIGS. 16A and 16B, strong supporter 700 and distal end 702 thereof are tube shaped defining a lumen (not referenced) running therethrough.

Curved supporter recess 704 is an opening at the distal end of strong supporter enabling the curved supporter to pass therethrough. The cross section of curved supporter recess 704 snugly matches the cross section of the curved supporter. In the example set forth in FIGS. 16A and 16B, the cross section shape of curved supporter recess 704 (and of the curved supporter itself) is rectangular bar shaped having rounded corners.

The cross section of the curved supporter corresponds to that of curved supporter recess 704. In case the operator of the access system rotates any one of strong supporter 700 or the curved supporter, the other one is rotated as well. That is, when a torsional force is applied to either one of strong supporter 700 and the curved supporter, the supporter on which the torsional force is applied applies the same force on the other supporter via the snug coupling of the supporters. Thus, torsional deformation of the bar shaped curved supporter is prevented (or at least reduced).

As can be seen, in the example set forth in FIGS. 16A and 16B, curved supporter recess 704 is positioned off the central longitudinal axis of strong supporter 700 (i.e., non-concentric). In other words, curved supporter recess 704 is located at the periphery of the cross section of distal end 702 of strong supporter 704. As mentioned above (with reference to FIGS. 4B, 4E and FIG. 8), by being positioned off center, at the opposite direction from the bending direction of the access system (i.e., at the extrados), the curved path of the curved supporter has a larger radius of curvature than that of the longitudinal axis of the access system. Thereby, the strain applied onto curved supporter when extending beyond the length of strong supporter 700 is reduced.

Work channel recess 706 is another opening at the distal end 702 of strong supporter 700. Work channel recess 706, together with the lumen defined within strong supporter 700, are part of the work channel of the access system, through which access is provided into and out of the sinus cavity. For example, the work channel can provide access to a working tool, such as an optical sensor and an illumination fiber bundle, into the sinus cavity of the patient. The work channel can also enable fluids to be pumped into or out of the sinus cavity. The fluids go through the lumen of strong supporter 700, along the curved supporter, and through work channel recess 706. Thus, the internal volume of strong supporter 700 is utilized (i.e., for slidably passing the curved supporter, and for enabling a working tool or fluids, to pass therethrough), and thereby the dimensions of the access system can be reduced.

In this manner, fluids that pass through work channel recess 706 can then pass through the weak straight supporter and exit from the access system into the sinus cavity through a port in the distal end of the weak straight supporter. Thus, fluids can be passed from a container (i.e., located outside of the patient's body) into the target location at the sinus cavity (or from the target location to a container outside of the patient's body) through the access system while the access system is maintained in place. In other words, the operator does not have to insert and/or retract one or more supporters, tools or any other instruments into (or out of) the patient's body multiple times in order to pass the fluids.

In accordance with an alternative embodiment of the disclosed technique, strong supporter 700 includes therewithin two separate channels (i.e., lumens). The first lumen enfolds the curved supporter of the access system, and ends at curved supporter recess 704. The second lumen defines the work channel and ends at work channel recess 706. In this manner, the curved supporter is separated from the working channel for preventing the working tool, or the fluids, passing through the work channel from coming into contact with the curved supporter.

Figure 17A:
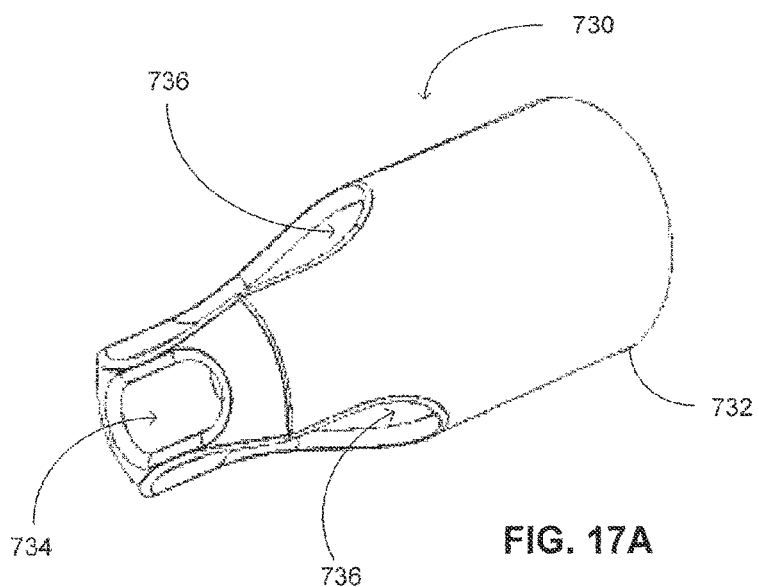
FIGS. 17A, 17B and 17C are schematic illustrations of a distal end of a strong straight supporter, constructed and operative with yet another embodiment of the disclosed technique.
Figure 17B:
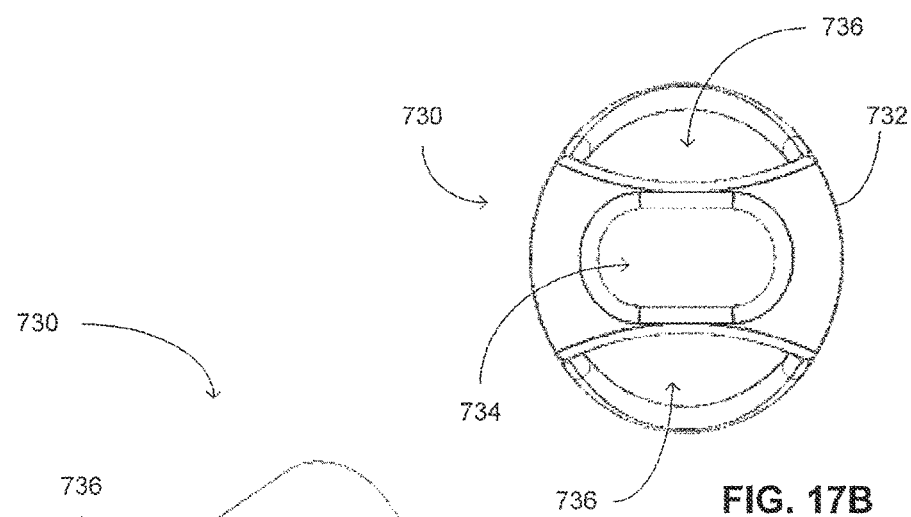
Figure 17C:
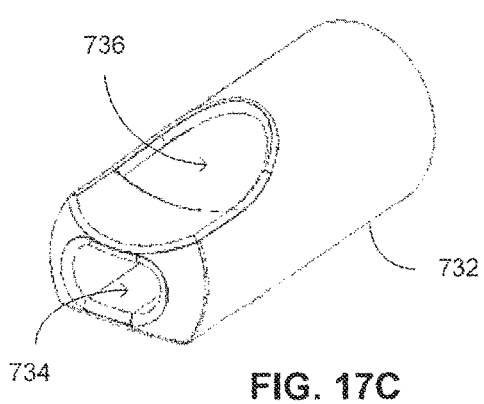

Reference is now made to FIGS. 17A, 17B and 17C, which are schematic illustrations of a distal end of a strong straight supporter, generally referenced 730, constructed and operative with yet another embodiment of the disclosed technique. FIG. 17A depicts the distal end of strong supporter 730 from a top view perspective. FIG. 17B depicts the distal end of strong supporter 730 from a front view perspective. FIG. 17C depicts the distal end of strong supporter 730 from an isometric perspective. Strong supporter 730 together with a weak supporter and a curved supporter (both not shown) form together a sinus access system (not shown—e.g., access system 250 of FIG. 4A). Strong supporter 730 includes a distal end 732, a curved supporter recess 734 and two work channel recesses 736.

In a similar manner to distal end 702 of FIGS. 16A and 16B, distal end 732 (or at least its proximal side) of strong supporter 730 has the same cross section as the rest of strong supporter 730 such that strong supporter 730 forms a continuous elongated body. As can be seen in FIGS. 17A-17C, strong supporter 730 and distal end 732 thereof are tube shaped defining a lumen (not referenced) running therethrough. Curved supporter recess 734 is substantially similar to curved supporter recess 704 of FIGS. 16A and 16B in terms of functionality. It is noted however, that curved supporter recess 734 is concentric with strong supporter 730 (i.e., is not located off-center).

In the example set forth in FIGS. 17A-17C, distal end 732 of strong supporter 730 includes two work channel recesses 736 positioned at opposite sides of distal end 732. Each of the work channel recesses 736 enables passage of a different working tool. For example, one work channel recesses 736 enables a camera to pass through the access system, and the other one work channel recess 736 enables an illumination fiber bundle to pass through the access system.

Each of the work channel recesses can also enable fluids to be pumped into or out of the sinus cavity. The fluids go through the lumen of strong supporter 730, along the curved supporter, and through the work channel recesses 736. Thus, similarly to the internal volume of strong supporter 700 depicted in FIGS. 16A-16B, the internal volume of strong supporter 730 is utilized (i.e., for slidably passing the curved supporter, and for enabling a working tool or fluids, to pass therethrough), and thereby the dimensions of the access system can be reduced. In this manner, fluids that pass through the work channel recesses 736 can then pass through the weak straight supporter and exit from the access system into the sinus cavity through a port in the distal end of the weak straight supporter. Thus, fluids can be passed from a container (i.e., located outside of the patient's body) into the target location at the sinus cavity (or from the target location to a container outside of the patient's body) through the access system while the access system is maintained in place. In other words, the operator does not have to insert or retract one or more supporters, tools or any other instruments to or from the patient's body multiple times in order to pass fluids thereto and/or therefrom.

As mentioned above, in some embodiments of the disclosed technique the weak supporter enfolds the other supporters of the access system. The weak distal end of the weak supporter can also be coupled with (or include) a functional distal head similar in structure and functionality to those described herein above with reference to FIGS. 16A-B and 17A-C. Furthermore, the functional distal head described in conjunction with FIG. 5 can also be structurally and functionally similar to the functional distal heads of FIGS. 16A-B and 17A-C.

Figure 18A:
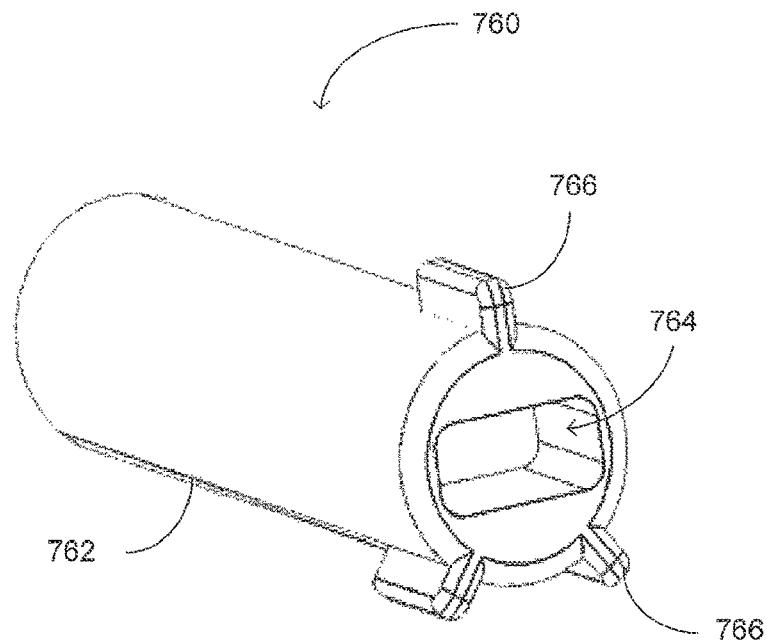
FIGS. 18A and 18B are schematic illustrations of a distal end of a strong straight supporter, constructed and operative with yet a further embodiment of the disclosed technique.
Figure 18B:
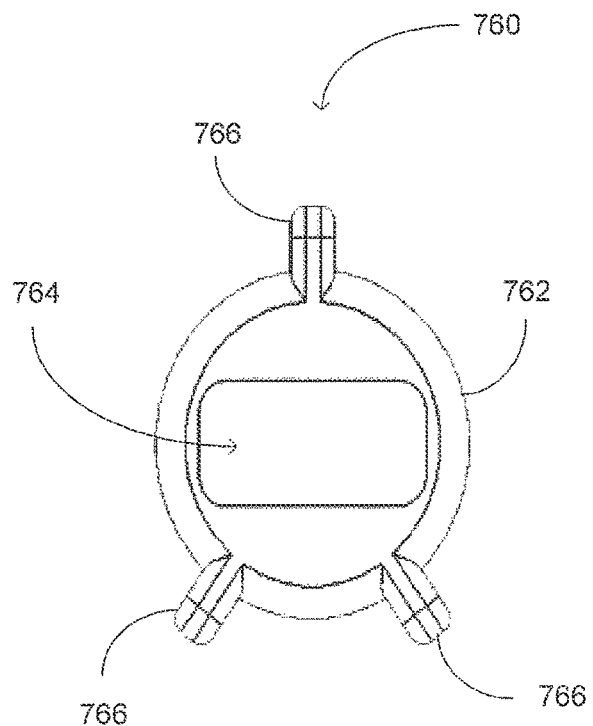

Reference is now made to FIGS. 18A and 18B, which are schematic illustrations of a distal end of a strong straight supporter, generally referenced 760, constructed and operative with yet a further embodiment of the disclosed technique. FIG. 18A depicts the distal end of strong supporter 760 from an isometric perspective. FIG. 18B depicts the distal end of strong supporter 760 from a front view perspective. Strong supporter 760 together with a weak supporter and a curved supporter (both not shown) form together a sinus access system (not shown—e.g., access system 250 of FIG. 4A). Strong supporter 760 includes a distal end 762, a curved supporter recess 764 and a plurality of radial protrusions 766.

Radial protrusions 766 extend radially from the external surface of strong supporter 760. The weak supporter (not shown) slidably enfolds strong supporter 760 and slides along radial protrusions 766. In this manner, an inner volume (i.e., intra-supporter volume) is formed between the internal surface of the weak supporter and the external surface of strong supporter 760. In other words, in case for example the weak supporter is in form of a coil, it enfolds (i.e., and hugs) the strong supporter and the radial protrusions, thereby an intra-volume is formed between the weak supporter and the strong supporter. The size of the intra-supporter volume is determined by the height (i.e., the length of the radial extension of the protrusions) of the radial protrusions.

The formed intra-supporter volume can be employed as a work channel or for enabling passage for fluids, into and out of, the sinus cavity. In the example, set forth in FIGS. 18A and 18B, the radial protrusion are fin shaped. Alternatively, any radial protruding element can function as the radial protrusions. The radial protrusions can be elongated and run along the length of the strong supporter, or can be short, as seen in FIG. 18A. The access system can include several sets of radial protrusions supporting the weak supporter that enfolds the strong supporter along the length of the strong supporter.

In this manner, fluids that pass through the intra-supporter volume can then further pass through the weak straight supporter (i.e., beyond strong supporter 760) and exit from the access system into the sinus cavity through a port in the distal end of the weak straight supporter. Thus, fluids can be passed from a container (i.e., located outside of the patient's body) into the target location at the sinus cavity (or from the target location to a container outside of the patient's body) through the access system while the access system is maintained in place. In other words, the operator does not have to insert and/or retract one or more supporters, tools or any other instruments to and/or from the patient's body multiple times in order to pass fluids thereto and/or therefrom.

As described herein above, according to some embodiments, the access system includes three supporters that form together a tortuous path (e.g., curved path), enabling the access system to access the sinus cavity of the patient. All supporters are advanced together until a first desired location, at which the access system should curve around anatomical obstacles for reaching the sinus. At the first desired location, the strong supporter is stopped, and the curved and weak supporters are advanced further. When the curved supporter extends beyond the strong supporter it regains its original curved shape, thereby producing the curved path of the access system. The radius of curvature of the path of the curved supporter might be different than that of the weak supporter. Therefore, the length of the path followed by each supporter (i.e., curved and weak) is different for completing the same curved angle. For example, due to different diameters of the supporters, or because of the different locations of the supporters within the access system (e.g., the curved supporter is at the extrados of the bend and the weak supporter is at the intrados). This can be analogized to athletes running around a circular (or oval) ring. An athlete running at the inner lane covers less distance than an athlete running at the outer lane.

Figure 19:
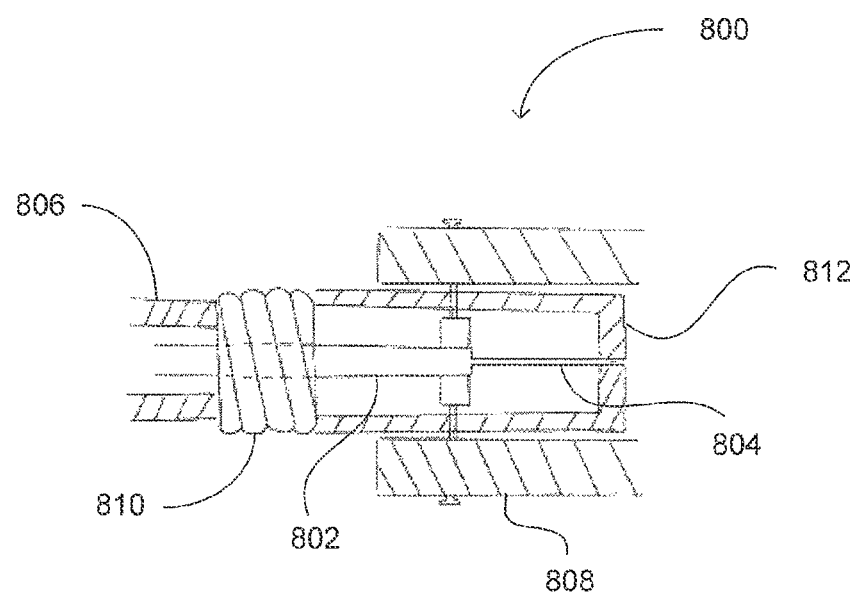
FIG. 19 is a schematic illustration of an access system, constructed and operative with yet another embodiment of the disclosed technique.

In case the operator advances the curved supporter and the weak supporter the same distance together (e.g., by pushing only one of the supporters), a compensating element can be coupled between the supporters for coordinating their advancement along the curved path, such that both supporters complete the same curve angle together. Reference is now made to FIG. 19, which is a schematic illustration of an access system, generally referenced 800, constructed and operative with yet another embodiment of the disclosed technique. Access system 800 includes a strong supporter 802, a curved supporter 804, a weak supporter 806, a housing 808, a compensating element 810, and a curved supporter coupler 812. Strong supporter 802, curved supporter 804 and weak supporter 806 are slidably coupled with each other. In a folded configuration of access system 800, housing 808 houses (at least in part) supporters 802, 804 and optionally 806. Supporters 802, 804 and 806 can extend distally out of housing 808 when inserted into the body of the patient. Compensating element 810 is coupled between curved supporter 804 and weak supporter 806. In the example set forth in FIG. 19, one end of compensating element 810 is coupled with weak supporter 806, and the opposite end of compensating element 810 is coupled with curved supporter 804, via curved supporter coupler 812.

Compensating element 810 can be for example, a coil, a biasing spring, or a stretchable wire. Alternatively, the compensating element can be formed from other components and elements for coordinating the movement of the curved supporter and the weak supporter across the curved path (e.g., gears). Alternatively, the compensating element can be accommodated in the housing 808. In the example set forth in FIG. 19, compensating element 810 is a spring (i.e., compensating spring 810). Compensating spring 810 enables simultaneous and coordinated movement of both curved supporter 804 and weak supporter 806.

Initially, when all supporters are overlapped (i.e., in a straight position), compensating spring 810 is loaded (i.e., preloaded). As curved supporter 804 advances distally, compensating spring 810 becomes unloaded, enabling the simultaneous and coordinated movement of the two supporters (i.e., curved and weak). As mentioned above, when both curved supporter 804 and weak supporter 806 are pushed together, each follows a different path and therefore, covers a different distance (i.e., for the same curve angle). Thereby, by pushing both supporters, one would advance further than the other. Compensating spring 810 compensates for the different paths followed by the supporters and enables both supporters to be advanced in a coordinated fashion. In summation, the function of the compensating element can be analogized to the function of a car differential that coordinates the rotations of the wheels during turns, thereby compensating for the different distances covered by the wheels during turns.

When the operator completes the curving of the access system, and wishes to advance the weak supporter beyond the curved supporter, the operator employs a release mechanism (not shown) for releasing compensating spring 810 from at least one of the supporters, thereby enabling advancement of only the weak supporter. The release mechanism can be formed of components, such as wires, piezoelectric elements, and the like.

Herein below additional features of the disclosed technique are detailed. In accordance with another embodiment of the disclosed technique, the access system (i.e., including the strong, curved, and weak supporters) may be accommodated within a housing (not shown) so that its components would be concealed from the patient. The housing includes a distal port through which the access system exits the housing and can be inserted into the body of the patient. The operator places the housing such the distal port thereof is located adjacently to the nostril of the patient, and the access system can be pushed via the nostril into the sinus cavity of the patient. When the procedure is done, the operator retracts the access system into the concealing housing, and only then the operator removes the housing from the patient. In this manner, the patient can only see the concealing housing, thereby, relieving her fears (i.e., which might be aroused when seeing the mechanical construction of the access system).

In accordance with a further embodiment of the disclosed technique, and as mentioned above, a camera is coupled with the access system. The camera can be coupled at the distal end of the access system (e.g., coupled to the functional distal head of the access system—e.g., functional head 304 of FIG. 5). In this manner, the operator can view the route ahead of the access system during the procedure. The camera dimensions can be, for example, about 1.5 (length)× 1×1 mm. Alternatively, the camera can be coupled a bit proximally (e.g., a few millimeters) to the distal end of the access system. The access system can include more than a single camera for covering a wider field of view (e.g., imaging opposite directions), or for stereoscopic imaging. The camera is coupled to a plurality of wires (e.g., electrical wires) configured to transfer signals from the camera to other electrical components, located proximally to the camera and possibly outside of the patient (e.g., a processor and a sampler).

The access system can further include illumination means (i.e., illumination devices) for illuminating the surrounding of the access system for the camera. The illumination devices can be, for example, optical fibers coupled to an external light source. The flexibility of the optical fiber enables it to conform to the bent path of the access system. According to some embodiments, the illuminating devices can further include lenses, prisms, reflectors, deflectors, optical couplers, and other optical components that can transmit light from an external light source through the access system.

For example, the access system can include a distal camera and two fiber bundles position on either side. The camera wiring and the illumination bundles are passing via the work channel of the access system (i.e., or via separate work channels). The optical fibers can be made of plastic (e.g., PMMA). The diameter of the optical fibers may be in the range of about 150 µm-500 µm, and preferably of about 250 µm.

The optical fibers and the camera wires are arranged so that they are not harmed (e.g., stretched, torn, broken) during the insertion and flexion of the access system. The optical fibers and the camera wires are preferably located at the side of the access system that is close to the bend in the access system for shortening their path, and avoiding unnecessary stretch. That is, the optical fibers and the camera wires are passed along the shortest peripheral curvature (i.e., internal curvature) of the access system. Coupling the camera wires along this internal curvature may provide further mechanical strengthening to the supporters' structure. For example, the un-stretchable camera wires limit the bending of the access system. In other words, the optical fibers and the camera wires are preferably positioned at, or toward, the intrados of the bend of the access system.

Alternatively, the optical fibers can be positioned toward the extrados of the curved path of the access system. In this manner, the radius of curvature of the optical fibers is enlarged for the same curved path of the access system. Thereby, the amount of light that escapes the optical fibers at the curve is decreased. In other words, the flexion of the optical fibers is reduced for reducing the amount of escaping light. For allowing the optical fibers to be positioned toward the extrados, without stretching the fibers, the fibers may be loose when the curved supporter is overlapped with the strong supporter and is straightened thereby.

In accordance with yet another embodiment of the disclosed technique, the camera (i.e., or cameras or other optical sensors) can be coupled to one or more image processors for handling the acquired image signals. For example, the image processor can compensate for the maneuvers of the access system (i.e., and therefore of the camera) by rotating the image, inverting the image, transposing the image, and the like. For instance, when the operator pushes the curved supporter beyond the strong supporter such that the access system bends at an angle of 120 degrees, and the camera is therefore partially inverted, the image processor can perform image inversion for compensating for the camera inversion.

According to some embodiments, the handling of the acquired image signals may be carried out automatically or semi-automatically (i.e., the operator is partially involved in operation), for example, based on additional signals generated by one or more sensors (e.g., an accelerometer or a position sensor located in the access system). Alternatively, the image handling may be controllable by the operator (i.e., manual handling). The handling of the image may further include controlling the illumination devices (e.g., controlling the amount of light). Controlling any of the camera, image signals and illumination may be carried out (at least partially) via a user interface (e.g., button, switch, knob, touch-sensitive screen) located in a housing (e.g., handle) of the access system.

In accordance with yet a further embodiment of the disclosed technique, additional devices can be externally coupled to the access system and thereby be guided toward, or into, the sinus cavity (i.e., add-on devices). The add-on devices can be coupled, for example, distally to (or at the vicinity of) the distal head of the access system. The add-on device can be coupled, for example, by employing a grip. The add-on devices can be, for example, a swab for collecting tissues, a needle for injecting a fluid (e.g., therapeutic fluid or a drug), a pincer-like head for inserting or removing pads or bandages into the patient's body, and the like.

The add-on devices can be employed for performing actions on the way to the sinus cavity, such as local anesthetic injection, or placement or removal of bandages.

In the examples set forth herein above, various access systems were presented. The access systems are directed at accessing the nasal cavity and paranasal sinuses of a patient. Additionally, the access systems can be employed for inserting a working tool via the access system. It is noted that in accordance with the disclosed technique, the access system should be at least partially multi-usage. That is, at least some portions of the access system should be re-used by the operator for accessing the paranasal sinuses of different patients or of the same patient at different times. Therefore, external portions (e.g., sleeves or sheathes) of the access system should be disposable and be disposed of after each user. Alternatively, the external sheathes or sleeves of the access system are disinfected between patients. In either case, the external sheath or sleeve of the access system is pushed by the operator all the way into the sinus cavity. In particular, an access device in which the external sheath is held at some point along the way and an internal element is pushed further into the sinus cavity would force the operator to disinfect (or dispose of) not only the external sheath but also that internal element, thereby increasing the costs of the each access.

In the description herein above the disclosed technique was employed for accessing the nasal and sinus cavities of a patient. Alternatively, the systems and methods of the disclosed technique can be employed for accessing other cavities within the body the patient, or other cavities in other environments, which can only be accessed in a curved tortuous path. For example, other areas of the Ear, Nose and Throat (ENT) field (e.g., ears, throat, esophagus, larynx), abdominal cavities, thoracic cavities, reproductive system, urinary system, gastric system, brain tissue, and the like.

It will be appreciated by persons skilled in the art that the disclosed technique is not limited to what has been particularly shown and described hereinabove. Rather the scope of the disclosed technique is defined only by the claims, which follow.

The invention claimed is:

1. A device for accessing and visualizing a paranasal sinus cavity of a patient, the device comprising:
   an outer weak straight supporter having a distal end with a first rigidity;
   an inner curved supporter having a distal curved portion with a second rigidity greater than the first rigidity, wherein at least said distal curved portion has a non-round cross-sectional shape;
   a middle strong straight supporter slidably disposed between said outer weak straight supporter and said inner curved supporter, at least a distal portion of said middle strong straight supporter having a third rigidity greater than the second rigidity and a recess with a cross-sectional shape that matches said non-round cross-sectional shape of said distal curved portion of said inner curved supporter, to allow at least said distal curved portion to pass therethrough; and
   a camera attached to said distal end of said outer weak straight supporter,
   wherein said distal curved portion of said inner curved supporter is configured to extend distally out of said middle strong straight supporter, such that said distal curved portion assumes a curved shape, and
   wherein said outer weak straight supporter is configured to be pushed over and distally beyond said distal curved portion of said inner curved supporter, such that an overlapped portion of said outer weak straight supporter conforms to the curved shape of said distal curved portion, and a distal, non-overlapped portion of said weak straight supporter is straight.

2. The system of claim 1, wherein an outer diameter of said outer weak straight supporter is one of continuous or constant across a length of said outer weak straight supporter.

3. The device of claim 1, wherein said outer weak straight supporter, said inner curved supporter and said middle strong straight supporter are concentrically coupled to one another.

4. The device of claim 1, wherein a width of said non-round cross section of said curved portion is defined as a dimension extending perpendicularly to the curved shape of said distal curved portion, and a height of said non-round cross section is defined as a dimension extending radially to said curved shape of said distal curved portion, said width of said non-round cross section of said curved portion being larger than said height of said non-round cross section of said curved portion.

5. The device of claim 1, further comprising wires coupled with said camera for transferring image signals, wherein said wires are positioned at an intrados of a bend formed by said device.

6. The device of claim 5, further comprising illuminating fibers positioned at said intrados of said bend formed by said device.

* * * * *